United States Patent
Avkin-Nachum

(10) Patent No.: US 9,611,473 B2
(45) Date of Patent: Apr. 4, 2017

(54) DOUBLE-STRANDED NUCLEIC ACID COMPOUNDS

(71) Applicant: QUARK PHARMACEUTICALS, INC., Fremont, CA (US)

(72) Inventor: Sharon Avkin-Nachum, Nes Zionna (IL)

(73) Assignee: QUARK PHARMACEUTICALS, INC., Fremont, CA (US)

( * ) Notice: Subject to any disclaimer, the term of this patent is extended or adjusted under 35 U.S.C. 154(b) by 0 days.

(21) Appl. No.: 14/417,796

(22) PCT Filed: Sep. 12, 2013

(86) PCT No.: PCT/US2013/059345
§ 371 (c)(1),
(2) Date: Jan. 28, 2015

(87) PCT Pub. No.: WO2014/043291
PCT Pub. Date: Mar. 20, 2014

(65) Prior Publication Data
US 2015/0259676 A1    Sep. 17, 2015

Related U.S. Application Data

(60) Provisional application No. 61/699,882, filed on Sep. 12, 2012.

(51) Int. Cl.
*C12N 15/113* (2010.01)
*A61K 31/122* (2006.01)
*A61K 47/48* (2006.01)

(52) U.S. Cl.
CPC ...... *C12N 15/113* (2013.01); *A61K 47/48023* (2013.01); *C12N 2310/11* (2013.01)

(58) Field of Classification Search
None
See application file for complete search history.

(56) References Cited

U.S. PATENT DOCUMENTS

2006/0035815 A1    2/2006    Chen et al.

FOREIGN PATENT DOCUMENTS

WO    WO 2011/123468 A1    10/2011

OTHER PUBLICATIONS

Kubo, JP 2009106165, May 21, 2006, machine translation.*
Kubo, Biochemical and Biophysical Research Communications 426 (2012) 571-577.*
Pedruzzi, Molecular and Cellular Biology, Dec. 2004, p. 10703-10717.*
Kubo T. el al.:"Lipid-Conjugated 27-Nucleotide Double-Stranded RNAs with Dicer-Substrate Potency enhance RNAi-Mediated Gene Silencing", Mol. Pharmaceutics, vol. 9, Apr. 11, 2012 (Apr. 11, 2011), pp. 1374-1382.

* cited by examiner

*Primary Examiner* — Layla Berry
(74) *Attorney, Agent, or Firm* — JMB Davis Ben-David

(57) ABSTRACT

The present invention provides double-stranded RNA (dsRNA) compounds comprising a sense and antisense strand, wherein at least one strand is conjugated to a moiety comprising a phenyl hydrocarbyl group, pharmaceutical compositions comprising same and uses thereof.

19 Claims, 12 Drawing Sheets

DOUBLE-STRANDED NUCLEIC ACID COMPOUNDS

RELATED APPLICATIONS

This is the U.S. National Stage of International Application No. PCT/US2013/059345, filed Sep. 12, 2013, which was published in English under PCT Article 21(2), which in turn claims the benefit of U.S. Provisional Application Ser. No. 61/699,882 filed Sep. 12, 2012 entitled "Double-Stranded Nucleic Acid Conjugates," which is incorporated herein by reference in its entirety and for all purposes.

FIELD OF THE INVENTION

The present invention provides double-stranded RNA (dsRNA) compounds comprising a sense and antisense strand, wherein at least one strand is conjugated to a moiety comprising a phenyl hydrocarbyl group, pharmaceutical compositions comprising same and uses thereof.

BACKGROUND OF THE INVENTION

Small interfering RNAs (siRNAs) are widely used to study gene function owing to the ease with which they silence target genes, and there is considerable interest in their potential for therapeutic applications. siRNAs have entered human clinical trials in various disease areas. However, rapid acceptance of the use of siRNAs has been accompanied by recognition of several hurdles for the technology, including a lack of specificity. Off-target activity may complicate the interpretation of phenotypic effects in gene-silencing experiments and can potentially lead to unwanted toxicities.

PCT Patent Publication Nos. WO 2008/104978, WO 2009/044392 and WO 2011/066475 to the assignees of the present invention and hereby incorporated by reference in their entirety, disclose siRNA structures.

Oligonucleotide conjugates are referred to in, inter alia, U.S. Pat. Nos. 6,783,931; 6,919,439 and 7,235,650.

U.S. Pat. No. 6,783,931 discloses nucleosides and oligonucleosides functionalized to include alkylamino functionality, and derivatives thereof, and further discloses steriods, reporter molecules, reporter enzymes, lipophilic molecules, peptides or proteins attached to the nucleosided through the alkylamino group.

U.S. Pat. Nos. 6,919,439, 7,235,650 disclose linked nucleosides having at least one functionalized nucleoside that bears a substituent such as a steroid molecule, a reporter molecule, a non-aromatic lipophilic molecule, a reporter enzyme, a peptide, a protein, a water soluble vitamin, a lipid soluble vitamin, an RNA cleaving complex, a metal chelator, a porphyrin, an alkylator, a pyrene, a hybrid photonuclease/intercalator, or an aryl azide photo-crosslinking agent exhibiting increased cellular uptake and other properties.

US Patent Publication No. 2010/0172844 and Dumelin, et al. (Angew. Chem. Int. Ed. 2008, 47:3196-3201) relate to portable albumin binders and drug conjugates comprising same.

There remains an unmet need in the art for new compositions and methods that minimize, alter, or eliminate off-target effects.

SUMMARY OF THE INVENTION

The present invention provides double-stranded RNA (dsRNA) compounds comprising a sense and antisense strand, wherein at least one strand is covalently bound to a phenyl hydrocarbyl moiety (PHM), pharmaceutical compositions comprising same and uses thereof.

The present invention, in some embodiments, provides active and nontoxic therapeutic dsRNA compounds having at least one of reduced off-target activity, extended plasma residency, beneficial biodistribution and cell-targeting features.

In some embodiments, the present invention provides double-stranded RNA (dsRNA) compounds having improved specificity and efficacy in mediating silencing of a target gene. In particular, the present invention provides dsRNA compounds, which, in some embodiments, have decreased off-target silencing activity and uses thereof in decreasing silencing of an inadvertent target by the dsRNA. The present invention further provides methods of using the dsRNA compounds as therapeutic agents. Importantly, The present invention addresses the issue of specificity by providing non-toxic therapeutic double-stranded RNA (dsRNA) compounds that can increase dsRNA specificity without impairing its on-target activity.

The present invention is based, in part, on the surprising discovery that compounds comprising dsRNA oligonucleotides conjugated at the 5' or 3' terminus of the sense and/or antisense strand to a moiety comprising a phenyl hydrocarbyl group display increased specificity and decreased off-target silencing activity as compared to non-conjugated dsRNA oligonucleotides. Importantly, the dsRNA compounds were found to have increased biological stability while retaining and in some cases improving their on-target gene silencing activity. Additionally, the dsRNA compounds of the present invention did not cause any in vivo immunostimulatory activity and their biodistribution was similar to that of the unconjugated dsRNA counterparts.

In one aspect, the present invention provides a double-stranded ribonucleic acid (dsRNA) compound comprising a sense strand and an antisense strand wherein the sense strand, the antisense strand or both are covalently attached directly or via a linker to a moiety comprising a phenyl hydrocarbyl group, the moiety is represented by the general formula I:

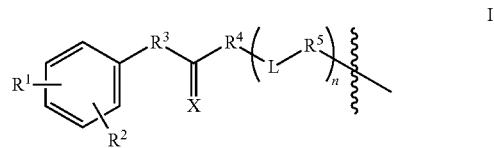

wherein $R^1$ and $R^2$ each is independently selected from the group consisting of H, halogen, $C_1$-$C_{10}$ hydrocarbyl group, $OR^6$, $OCOR^6$, $COOR^6$, $CH_2OR^6$, $CHO$, $COR^6$, $NR^6R^7$ and $SR^6$; or $R^1$ and $R^2$ together with the carbons to which they are attached form a saturated or unsaturated cyclic $C_3$-$C_8$ hydrocarbyl ring optionally interrupted by up to 2 heteroatoms selected from oxygen, nitrogen or sulfur and the ring is optionally substituted by up to 3 groups independently selected from the group consisting of halogen, $C_1$-$C_3$ hydrocarbyl group, $OR^6$, $OCOR^6$, $COOR^6$, $CH_2OR^6$, $CHO$, $COR^6$, $NR^6R^7$, $SR^6$, $=O$, $=S$ and $=NH$;

$R^3$ is a $C_1$-$C_8$ hydrocarbyl group optionally interrupted by up to 2 heteroatoms selected from oxygen, nitrogen or sulfur;

$R^4$ is NH, O, S or $CR^6R^7$;

X is O or S;

n is an integer selected from 0-10;

each L in each (L-R$^5$) groups is independently selected from the group consisting of a peptidyl chain of up to 12 amino acid residues, —[CH$_2$—CH$_2$—O]$_m$—, —R$_8$O—; and a C$_1$-C$_{12}$ hydrocarbyl group optionally interrupted by up to 2 heteroatoms selected from O, N or S;

R$_8$ is a C$_1$-C$_{12}$ hydrocarbyl group optionally interrupted by up to 2 heteroatoms selected from O, N or S;

m is an integer selected from 1-10;

each R$^5$ in each (L-R$^5$) group is independently selected from the group consisting of —P(O)(R$^9$)—O—, —C(O)NH—, —O—, —NH—; —S—; —C(O)—; —NHCS—; —NHCO— and a single bond;

R$^6$ and R$^7$ are each independently selected from the group consisting of H and a C$_1$-C$_4$ hydrocarbyl group;

R$^9$ is selected from the group consisting of O$^-$, S$^-$, BH$_3^-$, NR$^6$R$^7$ and CH$_3$;

or a pharmaceutically acceptable salt thereof;

wherein the sense strand has sequence identity to a consecutive segment of a mRNA corresponding to a target gene.

According to some embodiments, the moiety of formula (I) is covalently bound directly or via a linker to a sugar moiety, backbone or base of a terminal nucleotide or nucleotide analog of the strand in which it is present. According to some embodiments, the moiety of formula (I) is covalently bound directly or via a linker at the 3' terminal or 5' terminal nucleotide or nucleotide analog of the sense strand or at the 3' terminal nucleotide or nucleotide analog of the antisense strand directly or via a linker linking the terminal nucleotide to the moiety of formula (I). According to some embodiments, the moiety of formula (I) is covalently bound at the 5' terminal nucleotide of the sense strand. According to some embodiments, the moiety of formula (I) is covalently bound at the 3' terminal nucleotide of the sense strand. According to additional embodiments, the moiety of formula (I) is covalently bound at the 3' terminal nucleotide of the antisense strand.

According to some currently preferred embodiments, X in formula (I) is O. According to some embodiments R$^4$ in formula (I) is NH.

According to some other currently preferred embodiments group R$^3$ in formula (I) is C3 alkyl.

According to some embodiments, groups R$^1$ and R$^2$ in formula (I), together with the carbons to which they are attached, form a substituted or unsubstituted C$_3$-C$_8$ cycloalkyl. According to some embodiments, groups R$^1$ and R$^2$ in formula (I) together with the carbons to which they are attached, form a C$_6$ cycloalkyl.

According to some embodiments, X in formula (I) is O, R$^4$ is NH, R$^3$ is C$_3$ alkyl and R$^1$ and R$^2$ together with the carbons to which they are attached, form a C$_6$ cycloalkyl, thereby forming together with the phenyl ring to which they are attached a 5,6,7,8-tetrahydronaphthyl moiety, the obtained moiety is represented by the general formula II:

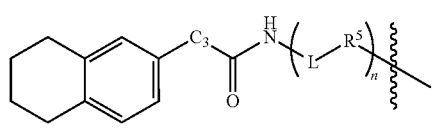

II

According to some embodiments, n is formula (I) or (II) is 0. According to some embodiments n=1. According to some embodiments n=1 and L is R$^8$O—. According to some embodiments, R$^8$ is a C$_2$-C$_8$ alkyl. According to some embodiments, n=1 and L is C$_6$O—. According to some embodiments n is 2-10. According to some embodiments, when n is bigger than 1, L may be same or different in each (L-R$^5$) group. According to some embodiments, n=2. According to some embodiments, n=2 and L is independently selected from R$^8$O— and —[CH$_2$—CH$_2$—O]$_m$—. According to some embodiments, n=2 and L is independently selected from C$_6$O— and —[CH$_2$—CH$_2$—O]$_3$—. According to some embodiments, X in formula (I) is O, R$^4$ is NH, R$^3$ is C$_3$ alkyl, L is a C$_6$O and n=1 with the proviso that when R$^1$ is H, R$^2$ is other than I.

According to some preferred embodiments, group R$^5$ in formula (I) is —P(O)(R$^8$)—O—.

According to some embodiments, when n is bigger than 1, R$^5$ may be same or different in each (L-R$^5$) group. According to some embodiments, when n is bigger than 1, at least one of the R$^5$ moieties is —P(O)(R$^8$)—O—.

According to some embodiments, X in formula (I) is O, R$^4$ is NH, R$^3$ is C$_3$ alkyl, L is a C$_6$O, n=1; R$^1$ and R$^2$ together with the phenyl ring to which they are attached form a 5,6,7,8-tetrahydronaphthalene moiety, R$^5$ is —P(O)(R$^8$)—O—, the phenyl hydrocarbyl moiety is directly linked to the 5' terminal nucleotide of the sense strand, the sense strand of the obtained double stranded ribonucleic acid compound is represented by the general formula III

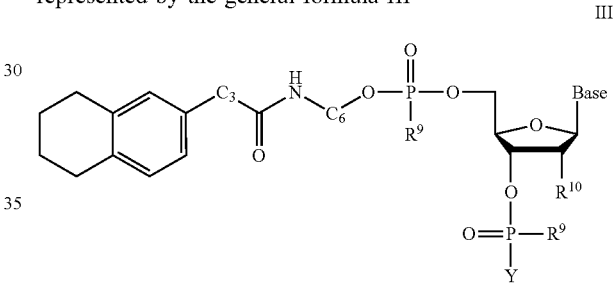

III wherein Y is an oligonucleotide of about 14 to 39 nucleotides in length, linked to the 5'O of the adjacent nucleotide;

wherein Base is adenine, guanine, cytosine, uracil or an analog thereof; and wherein R$^{10}$ is selected from the group consisting of H, OH, OR$^6$, NR$^6$R$^7$ and OR$^6$OR$^7$.

According to some embodiments, the moiety of formula (I) is directly bound to a sugar moiety, backbone or base moiety of a terminal nucleotide or nucleotide analog of the strand in which it is present.

According to some embodiments, the moiety of formula (I) is bound to a sugar moiety, backbone or base moiety of a terminal nucleotide or nucleotide analog of the strand in which it is present via a linker.

According to some embodiments, the linker may a carbon-based linker, a peptide linker, a nucleotide linker, an amido alkyl linker, a phosphodiester linker and a phosphorothioate linkage. According to some embodiments, the linker comprises a doubler or a trebler moiety.

According to some embodiments, the double-stranded ribonucleic acid compound of the invention is represented by general formula A:

(A) 5' (N)$_x$-Z 3' (antisense strand)

3' Z'-(N')$_y$-z" 5' (sense strand)

wherein each of N and N' is a ribonucleotide which may be unmodified or modified, or an unconventional moiety;

each of (N)x and (N')y is an oligoribonucleotide in which each consecutive N or N' is joined to the next N or N' by a covalent bond;

each of x and y is independently an integer between 15 and 40;

wherein at least one of Z, Z' and z" is present and comprises a moiety of formula (I) covalently attached directly or via a linker to the terminus of the strand in which it is present;

wherein:

(a) if z" is present, each of Z and Z' is independently present or absent, but if present comprises independently a moiety of formula (I), a delivery moiety or 1-5 nucleotides selected from the group consisting of consecutive nucleotides and consecutive non-nucleotide moieties or a combination thereof, covalently attached directly or via a linker at the 3' terminus of the strand in which it is present; or (b) if at least one of Z or Z' is present, z" may be present or absent, but if present comprises a moiety of formula (I), a delivery moiety or a capping moiety covalently attached directly or via a linker at the 5' terminus of the sense strand, and wherein the remaining Z or Z' is present or absent, but if present comprises independently a moiety of formula (I), a delivery moiety or 1-5 nucleotides selected from the group consisting of consecutive nucleotides and consecutive non-nucleotide moieties or a combination thereof, covalently attached directly or via a linker at the 3' terminus of the strand in which it is present; and wherein the sequence of (N')y is complementary to the sequence of (N)x; and wherein (N)x comprises an antisense that is complementary to about 15 to about 40 consecutive nucleotides in a target RNA.

According to some embodiments, each strand of the dsRNA is independently 18-40 nucleotides in length and the duplex is 18-40 nucleotides in length. In preferred embodiments, each strand of the dsRNA is independently 19-27 nucleotides in length and the duplex is 19-27 nucleotides in length, more preferably each strand of the dsRNA is independently 19 nucleotides in length and the duplex is 19 nucleotides in length. In various embodiments, the dsRNA is chemically synthesized.

According to some embodiments, the sequence of (N)x and the sequence of (N')y in the dsRNA of formula (A) are fully complementary. According to some embodiments, the sequence of (N)x is fully complementary to the sequence of a segment of a target mRNA.

According to alternative embodiments, the sequence of (N)x comprises a mismatch to the sequence of a target mRNA.

According to some embodiments, the sequences of (N)x and (N')y are unmodified. According to other embodiments, the sequence of (N)x and/or the sequence of (N')y are modified. According to some embodiments, at least one nucleotide of the sense stand or of the antisense strand comprises a modified nucleotide. In some embodiments, at least 2, at least 3, at least 4, at least 5, at least 6, at least 7, at least 8, at least 9, at least 10, or at least 11 nucleotides of the sense stand and/or of the antisense strand comprises a modified nucleotide. According to some embodiments, modification is selected from the group consisting of a sugar modification, a base modification and an internucleotide linkage modification.

According to some embodiments the double-stranded ribonucleic acid compound of general formula A comprises a z" moiety comprising a moiety of formula (I), the moiety of formula (I) is directly bound to the 5' terminal nucleotide of the sense strand. According to some embodiments the double-stranded ribonucleic acid compound of general formula A comprises a z" moiety comprising a moiety of formula (I), the moiety of formula (I) is bound to the 5' terminal nucleotide of the sense strand via a linker.

According to some embodiments, the double-stranded ribonucleic acid compound further comprises a delivery agent covalently bound directly or via a linker to one of the strands of the dsRNA. According to certain embodiments, the delivery agent is bound directly to a terminal nucleotide of one of the strands of the dsRNA. Alternatively, the delivery agent is bound to a terminal nucleotide of one of the strands of the dsRNA via a linker. The delivery agent may be a cell-targeting or a cell-internalization agent. According to some embodiments the delivery agent may be selected from the group consisting of a peptide, an antibody, an antibody fragment, a ligand, a receptor agonist, a receptor antagonist and a cell penetrating peptide (CPP). According to some embodiments, the delivery agent is selected from the group consisting of Naproxen, coenzyme Q10, tocopherol, bicultamide, a phospholipid, a retinoid, Vitamin D, derivatives thereof, and combinations thereof.

It is to be emphasized that when more than one moiety is bound to the dsRNA of formula (A) via a linker, the linker linking the different moieties to the dsRNA may be same or different and may be independently selected from the group consisting of carbon-based linker, a peptide linker, a nucleotide linker, an amido alkyl linker, a phosphodiester linker and a phosphorothioate linkage. The linkers may further comprise a doubler or a trebler moiety.

Preferred embodiments for double-stranded RNA compounds bound to a moiety of formula (I) and an optional delivery agent include the following options:

| Sense strand (N')y 5' terminus | Sense strand (N')y 3' terminus | Antisense strand (N)x 3' terminus |
|---|---|---|
| Moiety of formula (I) | — | — |
| — | Moiety of formula (I) | — |
| — | — | Moiety of formula (I) |
| Moiety of formula (I) | delivery agent | — |
| Moiety of formula (I) | — | delivery agent |
| — | Moiety of formula (I) | delivery agent |
| delivery agent | Moiety of formula (I) | — |
| delivery agent | — | Moiety of formula (I) |
| — | delivery agent | Moiety of formula (I) |
| Moiety of formula (I) | delivery agent | Moiety of formula (I) |
| Moiety of formula (I) | Moiety of formula (I) | delivery agent |
| delivery agent | Moiety of formula (I) | Moiety of formula (I) |

Each of the above options includes moieties bound directly or via a linker. Each of the options above represents a separate embodiment of the invention.

The double-stranded ribonucleic acid compounds of the invention are capable of interfering with the expression of specific target genes. According to some embodiments, the target gene is a human, bacterial or a viral target gene. According to some embodiments, the target gene is a human target gene selected from the group consisting of DDIT4, CDKN1B, RTP801 (REDD1), CASP2, p53, RhoA, MYD88, TLR2, TLR4, Nox3, Hes5, Hes3, CAPNS, REDD2, and a NOX gene selected from NOX1, NOX2, NOX3, NOX4, NOX5, DUOX1, DUOX2, NOXO1, NOXO2 (p47phox, NCF1), NOXA1, NOXA2 (p67phox, NCF2) and CYBA. According to certain embodiments, the human target gene is selected from the group consisting of RhoA, DDIT4, MYD88 and CDKN1B.

According to some embodiments the conjugation of a moiety of formula (I) to at least one of the terminal nucleotides of a dsRNA, imparts on the dsRNA at least one beneficial property selected from the group consisting of reducing off target activity, increasing serum stability, increasing serum circulation time, increasing bioavailability, decreasing serum clearance, improving biodistribution, increasing melting temperature, improving cellular uptake, reducing immunogenicity, improving endosomal release and increasing knock down activity when compared to unconjugated dsRNA counterparts. According to certain preferred embodiments, the conjugation of a moiety of formula (I) to the 5' terminal nucleotide of a sense strand of a dsRNA, reduces the off-target activity and increases the specificity of the dsRNA as compared to unconjugated dsRNA counterparts. According to additional preferred embodiments, the conjugation of a moiety of formula (I) to the 3' terminal nucleotide of the sense strand, the antisense strand or both, increases the serum stability of the dsRNA by protecting the dsRNA from degradation by nucleases as compared to unconjugated dsRNA counterparts. According to yet additional preferred embodiments, the conjugation of a moiety of formula (I) to the 3' or 5' terminal nucleotide of a sense strand, the 3' terminal nucleotide of the antisense strand or to any combination thereof, improves the circulation time of the conjugated dsRNA, increases its retention time and improves its tissue penetration capacity as compared to unconjugated dsRNA counterparts.

According to another aspect, the present invention provides a pharmaceutical composition comprising a effective amount of a double-stranded ribonucleic acid comprising a sense strand and an antisense strand wherein the sense strand, the antisense strand or both are covalently attached to a moiety of formula (I) and a pharmaceutically acceptable carrier. According to some embodiments, the pharmaceutical composition comprises the conjugated dsRNA in an amount effective to inhibit mammalian or non-mammalian gene expression.

According to another aspect, the present invention provides a method for treating or preventing the incidence or severity of a disease or condition and/or symptoms associated therewith in a subject in need thereof, the disease or condition and/or symptom associated therewith is associated with expression of a target gene, the method comprising administering to the subject the conjugated dsRNA compound as described herein or a pharmaceutical composition comprising same in an amount effective to prevent or treat the disease or condition.

According to some embodiments, the present invention provides a conjugated dsRNA as disclosed herein above or the pharmaceutical composition comprising same, for use in treating or preventing the incidence or severity of a disease or condition and/or symptoms associated therewith in a subject in need thereof.

Also provided is the use of the conjugated dsRNA compound as disclosed herein above or the pharmaceutical composition comprising same in the manufacture of a medicament for treating or preventing the incidence or severity of a disease or condition and/or symptoms associated therewith in a subject in need thereof.

According to some embodiments the disease or condition to be treated by the conjugated dsRNA of the invention is selected from the group consisting of hearing loss, acute renal failure (ARF), glaucoma, acute respiratory distress syndrome (ARDS) and other acute lung and respiratory injuries, ischemia-reperfusion injury following lung transplantation, ocular ischemic conditions including anterior ischemic optic neuropathy organ transplantation including lung, liver, heart, pancreas, and kidney transplantation and including DGF, nephro- and neurotoxicity, spinal cord injury, neurodegenerative disease or condition, pressure sores, age-related macular degeneration (AMD), dry eye syndrome, ION, oral mucositis, cancer and chronic obstructive pulmonary disease (COPD).

According to yet another aspect of the present invention, there is provided a method of producing a double-stranded ribonucleic acid compound having increased plasma stability, the method comprising covalently binding to the 3' terminal nucleotides of a sense strand, the antisense strand or both of the dsRNA compound, a molecule comprising a phenyl hydrocarbyl moiety of formula (I) as disclosed herein above, wherein the moiety of formula (I) is covalently bound directly or via a linker to a sugar moiety, backbone or base moiety of the terminal nucleotide, such that the dsRNA compound bound to the moiety of formula (I) has increased plasma stability relative to the plasma stability of unconjugated dsRNA counterparts.

According to a further aspect, the present invention provides a method of increasing the plasma stability of a double-stranded ribonucleic acid compound, the method comprising covalently binding to at least one terminal nucleotide of a sense strand or an antisense strand of the dsRNA compound, a molecule comprising a moiety of formula (I) as disclosed herein above, wherein the moiety of formula (I) is covalently bound directly or via a linker to a sugar moiety, backbone or base moiety of the 3' terminal nucleotide of the sense strand, the antisense strand or both, such that the dsRNA compound bound to the moiety of formula (I) has increased plasma stability relative to the plasma stability of an unconjugated dsRNA counterpart.

According to yet another aspect, the present invention provides a method of producing a double-stranded ribonucleic acid compound having decreased off-target silencing activity, the method comprising covalently binding to the terminal 5' nucleotide of a sense strand of a dsRNA compound, a moiety represented by the general formula (I) as disclosed herein above, such that the dsRNA compound bound to the moiety of formula (I) has decreased off-target silencing activity relative to the off-target silencing activity by unconjugated dsRNA counterparts.

According to a further aspect, the present invention provides a method for decreasing off-target silencing activity of an inadvertent target mRNA by a double stranded RNA compound, the method comprising covalently binding to a 5' terminus of a sense strand of the double stranded RNA compound, a molecule comprising a moiety represented by the general formula (I) as disclosed herein above, wherein the moiety of formula (I) is covalently bound directly or via a linker to a sugar moiety, backbone or base moiety of the 5' terminal nucleotide of the sense strand, such that the off-target silencing of the inadvertent target mRNA by the dsRNA compound bound to the moiety of formula (I) has decreased off-target silencing activity relative to the off-target silencing activity by an unconjugated dsRNA counterpart.

The present invention further provides a compound represented by the general formula IV:

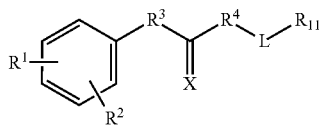

IV wherein $R^1$, $R^2$, $R^3$, $R^4$, X and L are as defined herein above;

$R^{11}$ is a functional group selected from the group consisting of phosphoramidite,

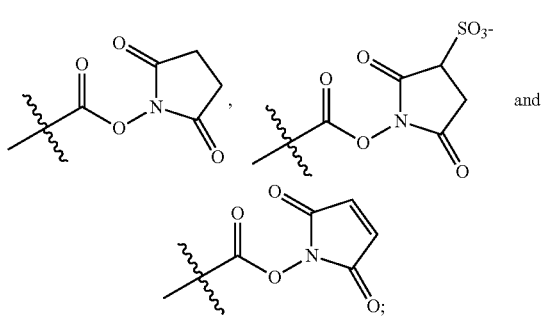

or a pharmaceutically acceptable salt thereof.

According to some embodiments, X in formula (IV) is O. According to some embodiments, $R^4$ in formula (IV) is NH. According to some currently preferred embodiments, there is provided a compound of formula (IV) wherein X is O and $R^4$ is NH.

According to some embodiments, $R^3$ in formula (IV) is a $C_3$ alkyl. According to some embodiments, L in formula (IV) is $R^8O$. According to some embodiments, $R^8$ is $C_6$ alkyl. According to some embodiments, L in formula (IV) is a $C_6$ alkyloxy (—C6O—). According to currently preferred embodiments, X in formula (IV) is O; $R^4$ is NH; $R^3$ is $C_3$ alkyl and L is a $C_6$ alkyloxy.

According to additional embodiments, groups $R^1$ and $R^2$ in formula (IV), together with the carbons to which they are attached, form a substituted or unsubstituted $C_3$-$C_8$ cycloalkyl. According to some embodiments, groups $R^1$ and $R^2$ in formula (IV) together with the carbons to which they are attached, form a $C_6$ cycloalkyl. According to some embodiments, $R^1$ and $R^2$ in formula (IV) together with the carbons to which they are attached, form together with the phenyl ring to which they are attached a 5,6,7,8-tetrahydronaphthyl group.

According to some embodiments, $R^{11}$ in formula (IV) is a phosphoramidite moiety of the formula —P(O$R^{12}$)N$R^{13}R^{14}$ wherein $R^{12}$ is selected from the group consisting of H or ($C_1$-$C_8$)alkyl substituted with a —CN group and each of $R^{13}$ and $R^{14}$ is independently selected from the group consisting of H and a $C_1$-$C_4$ hydrocarbyl group.

According to some preferred embodiments, X in formula (IV) is O, $R^4$ is NH, $R^3$ is $C_3$ alkyl, L is a $C_6$ alkyloxy, $R^1$ and $R^2$ together with the phenyl ring to which they are attached form a 5,6,7,8-tetrahydronaphthyl group, and $R^{12}$ is P(O$R^{13}$)N$R^{14}R^{15}$ wherein $R^{12}$ is cyanoethyl and $R^{13}$ and $R^{14}$ are both isopropyl groups, the obtained phenyl hydrocarbyl moiety is represented by the general formula V:

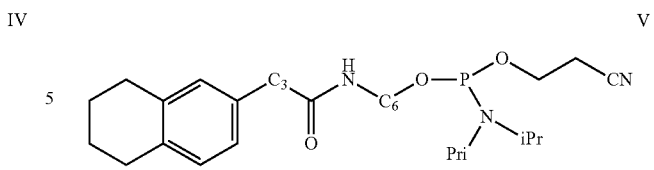

V

According to some embodiments, $R^{11}$ in formula (IV) is a NHS ester, selected from the group consisting of

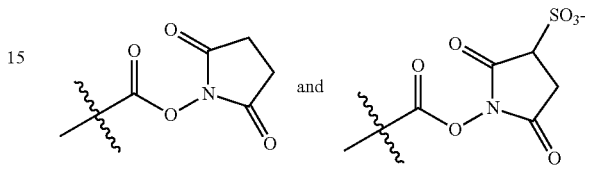

The methods, materials, and examples that will now be described are illustrative only and are not intended to be limiting; materials and methods similar or equivalent to those described herein can be used in practice or testing of the invention. Other features and advantages of the invention will be apparent from the following detailed description, and from the claims.

DETAILED DESCRIPTION OF THE INVENTION

Figure 1:
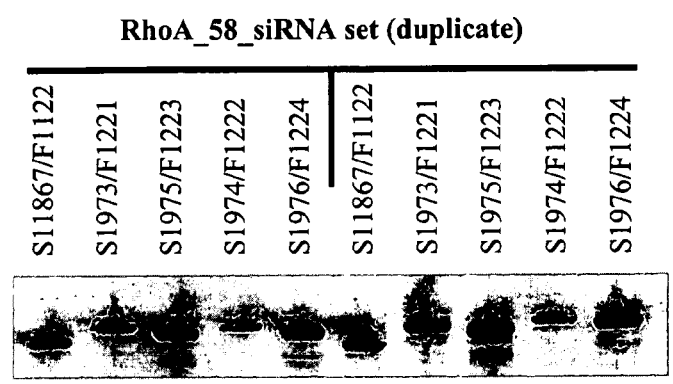
FIG. 1 depicts mobility of THNBC6 attached anti-sense strands in PAGE with denatured gel.

Provided herein are modified dsRNA compounds, also known as conjugates or conjugate molecules, which are capable of down regulating gene expression and are modified by attachment of a moiety comprising a phenyl hydrocarbyl group. In some embodiments a preferred phenyl hydrocarbon group comprises a 5,6,7,8-tetrahydronaphthyl group. The dsRNA conjugates of the present invention are active, nontoxic and exhibit beneficial properties including at least one of reduced off-target effect and/or increased affinity to RISC-AGO complex, altered biodistribution, increased melting temperature (Tm), increased serum circulation time, increased serum stability, improved cellular uptake, reduced immunogenicity, improved endosomal release, improved specific delivery to target tissue or cell, increased knock down activity in comparison to unconjugated counterparts. In some embodiments a preferred property of the dsRNA conjugate of the invention is reduced off-target effect. These conjugated dsRNA compounds of the invention are useful in the treatment of subjects suffering from diseases or conditions and or symptoms associated with such diseases or conditions in which down regulation or inhibition or attenuation of a target gene expression is beneficial.

In one aspect, the present invention provides a double-stranded ribonucleic acid (dsRNA) compound comprising a sense strand and an antisense strand wherein the sense strand, the antisense strand or both are covalently attached directly or via a linker to a moiety comprising a phenyl hydrocarbyl group represented by the general formula I:

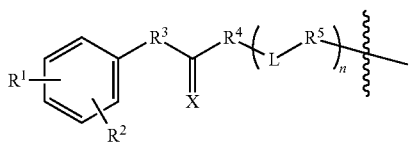

I wherein $R^1$ and $R^2$ each is independently selected from the group consisting of H, halogen, $C_1$-$C_{10}$ hydrocarbyl group, $OR^6$, $OCOR^6$, $COOR^6$, $CH_2OR^6$, CHO, $COR^6$, $NR^6R^7$ and $SR^6$; or $R^1$ and $R^2$ together with the carbons to which they are attached form a saturated or unsaturated cyclic C3-C8 hydrocarbyl ring optionally interrupted by up to 2 heteroatoms selected from oxygen, nitrogen or sulfur, the ring and is optionally substituted by up to 3 groups independently selected from the group consisting of halogen, $C_1$-$C_3$ hydrocarbyl group, $OR^6$, $OCOR^6$, $COOR^6$, $CH_2OR^6$, CHO, $COR^6$, $NR^6R^7$, $SR^6$, $=O$, $=S$ and $=NH$;

$R^3$ is a $C_1$-$C_8$ hydrocarbyl group optionally interrupted by up to 2 heteroatoms selected from oxygen, nitrogen or sulfur;

$R^4$ is NH, O, S or $CR^6R^7$;

X is O or S;

each L in each (L-$R^5$) group is independently selected from the group consisting of a peptidyl chain of up to 12 amino acid residues, —[$CH_2$—$CH_2$—$O$]$_m$—, a $C_1$-$C_{12}$ hydrocarbyl group optionally interrupted by up to 2 heteroatoms selected from O, N or S and —$R^8O$—;

$R^8$ is a $C_1$-$C_{12}$ hydrocarbyl group optionally interrupted by up to 2 heteroatoms selected from O, N or S;

n is an integer selected from 0-10;

m is an integer selected from 1-10;

$R^5$ is selected from the group consisting of —P(O)($R^9$)—O—, —C(O)NH—, —O—, —NH—; —S—; —C(O)—; —NHCS—; —NHCO— and a single bond;

$R^6$ and $R^7$ are each independently selected from the group consisting of H and a $C_1$-$C_4$ hydrocarbyl group;

$R^9$ is selected from the group consisting of O$^-$, S$^-$, $BH_3^-$, $NR^6R^7$ and $CH_3$;

or a pharmaceutically acceptable salt thereof;

wherein the sense strand has sequence identity to the segment of a mRNA corresponding to a target gene.

According to some embodiments, the moiety of formula (I) described herein can be incorporated into any double-stranded RNA and RNA-like molecule, e.g., an iRNA agent. The sense and antisense strands may include modifications at the 3' end and/or the 5' end and/or at any one of the intervening positions between the two ends of the strand. According to some embodiments, the moiety of formula (I) is covalently bound directly or via a linker to a sugar moiety, backbone or base of a terminal nucleotide or nucleotide analog of the strand in which it is present. According to some embodiments, the moiety of formula (I) is covalently bound directly at the 3' terminal or 5' terminal nucleotide or nucleotide analog of the sense strand or at the 3' terminal nucleotide or nucleotide analog of the antisense strand directly. According to some embodiments the moiety of formula (I) is covalently bound via a linker at the 3' terminal or 5' terminal nucleotide or nucleotide analog of the sense strand or at the 3' terminal nucleotide or nucleotide analog of the antisense, the linker links the terminal nucleotide to the moiety of formula (I). According to some embodiments, the moiety of formula (I) is covalently bound at the 5' terminal nucleotide of the sense strand directly or via a linker. According to some embodiments, the molecule comprising the moiety of formula (I) is covalently bound at the 3' terminal nucleotide of the sense strand directly or via a linker. According to additional embodiments, the moiety of formula (I) is covalently bound at the 3' terminal nucleotide of the antisense strand directly or via a linker.

According to some currently preferred embodiments, X in formula (I) is O. According to some embodiments $R^4$ in formula (I) is —NH—. According to some embodiments $R^4$ in formula (I) is —O—.

According to some embodiments $R^3$ in formula (I) is selected from a $C_2$ alkyl, a $C_3$ alkyl, a $C_4$ alkyl, a $C_5$ alkyl, a $C_6$ alkyl, a $C_7$ alkyl and a $C_8$ alkyl. Each possibility represents a separate embodiment of the invention. According to some embodiments $R^3$ in formula (I) is $C_3$ alkyl.

According to additional currently preferred embodiments, groups $R^1$ and $R^2$ in formula (I), together form a cyclic structure, said cyclic structure is preferably a linear or branched hydrocarbyl chain of 3-8 more preferably, 3-7, 3-6, 3-5, 3-4 or 4 carbon atoms bonded at two positions to the phenyl ring of formula (I), i.e. forming two bonds to said phenyl ring, such as to form a ring structure fused to said phenyl ring. Said cyclic structure is optionally interrupted by up to 2 heteroatoms. Said cyclic structure is optionally substituted by up to 4, alternatively up to 3, alternatively up to 2, alternatively substituted by one or none groups selected from F, Cl, Br, I, $C_1$-$C_3$ hydrocarbyl group, $OR^6$, $OCOR^6$, $COOR^6$, $CH_2OR^6$, CHO, $COR^6$, $NR^6R^7$, $SR^6$, $=O$, $=S$ and $=NH$. According to some preferred embodiments, groups $R^1$ and $R^2$ in formula (I) together with the phenyl ring to which they are attached form a 5,6,7,8-tetrahydronaphthalene moiety.

According to some embodiments, X in formula (I) is O, $R^4$ is NH, $R^3$ is $C_3$ alkyl and $R^1$ and $R^2$ together with the phenyl ring to which they are attached form a 5,6,7,8-tetrahydronaphthyl moiety, the obtained phenyl hydrocarbyl moiety is represented by the general formula II:

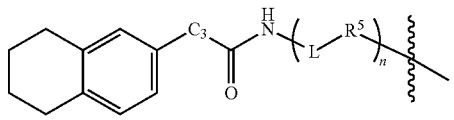

II

According to some embodiments, the phenyl hydrocarbyl moiety represented by the general formula II is covalently bound at the 3' terminal or 5' terminal nucleotide or nucleotide analog of the sense strand or at the 3' terminal nucleotide or nucleotide analog of the antisense strand directly or further via a first linker linking the terminal nucleotide to the phenyl hydrocarbyl moiety of formula (II).

According to some embodiments, n in formula (I) is 0. According to some embodiments, n in formula (I) is 1. According to some embodiments, n in formula (I) is 2. According to some embodiments, n in formula (I) is 3. According to some embodiments, n in formula (I) is 4-10. According to some embodiments, L in formula (I) is a $C_2$-$C_8$ alkyloxy. According to some embodiments, L is a —($CH_2$—$CH_2$—O)$_m$— group. According to some embodiments, L is a —($CH_2$—$CH_2$—O)$_m$— group, wherein m is selected from 1-9; alternatively, 1-8; alternatively; 1-7; alternatively, 1-6; alternatively, 1-5; alternatively, 1-4; alternatively, 1-3. According to some currently preferred embodiments, L is a $C_6$ alkyloxy. According to some embodiments n is 1 and L is a $C_6$ alkyloxy. According to some embodiments, $R^3$ in formula (I) is $C_3$ alkyl, L is a $C_6$ alkyloxy and n=1. According to some embodiments, n=2 and L is independently selected from $C_2$-$C_8$ alkyloxy and —[$CH_2$—$CH_2$—O]$_m$—. According to some embodiments, n=2 and L is independently selected from $C_6$ alkyloxy and —[$CH_2$—$CH_2$—O]$_3$—. According to some embodiments, X in formula (I) is O, $R^4$ is NH, $R^3$ is $C_3$ alkyl, L is a $C_6$ alkyl and n=1 with the proviso that when $R^1$ is H, $R^2$ is other than I. According to certain embodiments, X in formula (I) is O, $R^4$ is NH, $R^3$ is $C_3$ alkyl, n=2, and L is independently selected from $C_6$ alkyloxy and —[$CH_2$—$CH_2$—O]$_3$.

According to some embodiments $R^5$ is selected from the group consisting of —P(O)($R^9$)—O—, —C(O)NH—, —O—, —NH—; —S—; —C(O)—; —NHCS—; —NHCO— and a single bond. Each possibility represents a separate embodiment of the invention. According to some preferred embodiments, group $R^5$ in formula (I) is —P(O)($R^8$)—O—.

According to some embodiments, X in formula (I) is O, R4 is NH, $R^3$ is $C_3$ alkyl, L is a $C_6$ alkyloxy, n=1; $R^1$ and $R^2$ together with the phenyl ring to which they are attached form a 5,6,7,8-tetrahydronaphthalene moiety, $R^5$ is —P(O)($R^8$)—O—, the phenyl hydrocarbyl moiety is directly linked to the 5' terminal nucleotide of the sense strand, the obtained double stranded ribonucleic acid compound wherein the sense strand is represented by the general formula III:

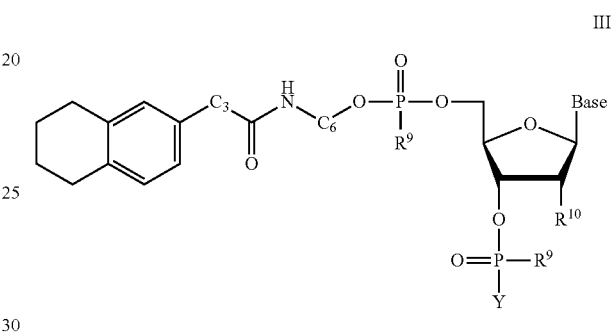

III wherein Y is an oligonucleotide of about 14 to 39 nucleotides in length, linked to the 5'O of the adjacent nucleotide;

wherein Base is adenine, guanine, cytosine, uracil or an analog thereof; and wherein $R^{10}$ is selected from the group consisting of H, OH, $OR^6$, $NR^6R^7$ and $OR^6OR^7$.

Additional specific examples of the compounds of formula (I) include but are not limited to:

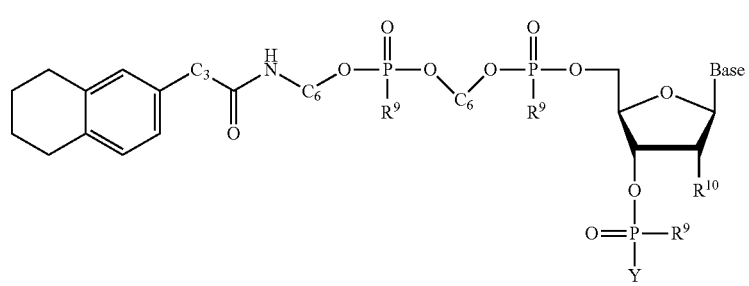

IIIa

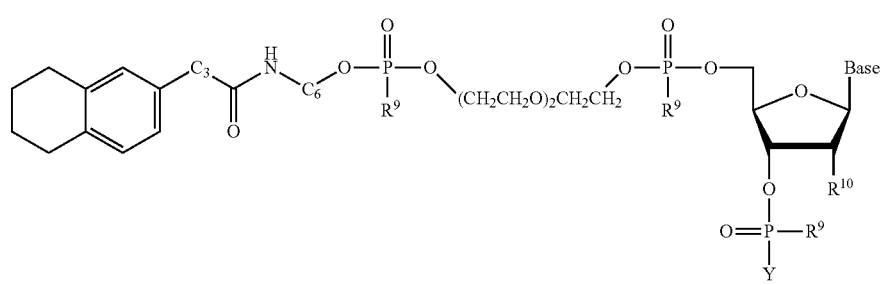

IIIb

According to some embodiments, the moiety of formula (I) covalently attached to the 3' or 5' terminal nucleotide or nucleotide analogous of the sense or antisense strands may referred to as a capping moiety.

The moiety of formula (I) may be coupled to the nucleic acid molecules either directly, i.e through a functional group present in one or more of the nucleotides (base, sugar or linkage), or via a linker further introduced into the moiety of formula (I), the nucleic acid molecule or both the moiety of formula (I) and the nucleic acid molecule.

According to some embodiments provided herein is a conjugate comprising a nucleic acid molecule covalently linked to a moiety of formula (I), wherein $R^3$ is a $C_3$ alkyl, e.g. a moiety comprising a 4-phenylbutanoic acid derivative. According to some preferred embodiments, the conjugate comprises a nucleic acid molecule covalently linker to a moiety of formula (II), e.g. a moiety comprising a 5,6,7,8-tetrahydro-2-naphthalenebutanoic (THNB) acid derivative. A non-limiting example of compound comprising the moiety of formula (I) that may be used for linking the moiety of formula (I) to a terminal nucleotide of the sense or antisense strands is the compounds represented by formula V:

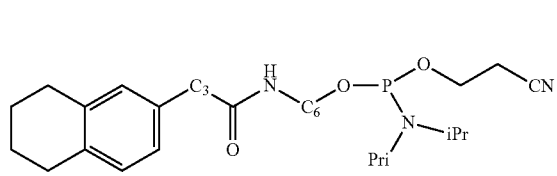

V

Conjugation is achieved, for example, by coupling the phosphoramidite of formula (V) to the growing oligonucleotide chain under standard phosphoramidite coupling conditions.

Another non-limiting example of a compound comprising the moiety of formula (I) that may be used for linking the moiety of formula (I) to a terminal or internal nucleotide of the sense or antisense strands is the following compound VI.

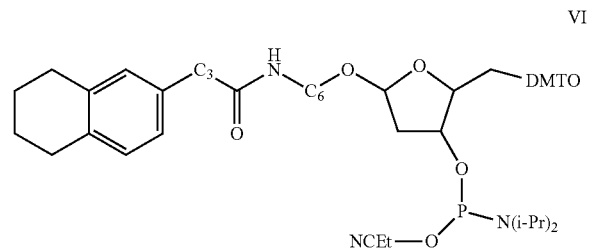

VI

According to some embodiments, the compound of formula VI comprises the linker moiety represented by formula (II) further connected to a linking moiety comprising a sugar moiety substituted with a phosphoramidite.

According to some embodiments, the compounds of formula (IV) wherein $R^{11}$ represents a phosphoramidite may be prepared by known in the art methods for the preparation of phosphoramidites, for example as disclosed in US2012/0035362.

DEFINITIONS

For convenience certain terms employed in the specification, examples and claims are described herein.

It is to be noted that, as used herein, the singular forms "a", "an" and "the" include plural forms unless the content clearly dictates otherwise.

Where aspects or embodiments are described in terms of Markush groups or other grouping of alternatives, those skilled in the art will recognize that the invention is also thereby described in terms of any individual member or subgroup of members of the group.

A "conjugate" or "conjugate molecule" or a "conjugate compound" as used herein refers to a molecule that comprises two (or more) chemical moieties, which are covalently linked. In specific embodiments a conjugate or conjugate molecule includes a nucleic acid molecule covalently bound, joined or linked to a moiety of formula (I) as described hereinabove. In some embodiments the moiety of formula (I) and/or nucleic acid molecule may be further linked to at least one additional molecule such as a NSAID; a phospholipid; a dietary supplement; a vitamin; a human serum albumin (HSA) binding agent (HAB); an androgen or estrogen receptor agonist or antagonist; an anti-cancer agent; a peptide; a sigma receptor agonist; or a carbohydrate (simple or complex).

A "delivery agent" as used herein refers to a molecule used to covalently modify a nucleic acid of the present invention, the resultant molecule possessing one or more of increased bioavailability, improved biodistribution, increased melting temperature, increased serum circulation time, increased serum stability, decreased serum clearance, improved cellular uptake, improved endosomal release, improved specific delivery to target tissue or cell and increased knock down activity as compared with a nucleic acid lacking said delivery agent. Without wishing to be bound to theory the delivery agent facilitates delivery of the conjugate into a biological system, such as a cell and or facilitates endosomal escape. For example, the additional molecule attached to the conjugate molecule is a polyethylene glycol, or a peptide, aptamer, antibody or ligand for a cellular receptor.

An "inhibitor" as used herein refers to a compound, which is capable of reducing (partially or fully) the expression of a gene or the activity of the product of such gene to an extent sufficient to achieve a desired biological or physiological effect. The term "inhibitor" as used herein refers to a nucleic acid inhibitor such as siRNA, shRNA, synthetic shRNA; and miRNA. The term "inhibit" as used herein refers to reducing the expression of a gene or the activity of the product of such gene to an extent sufficient to achieve a desired biological or physiological effect. Inhibition is either complete or partial. As used herein, the term "inhibition" of a target gene means inhibition of the expression (transcription or translation) of a target gene or the polypeptide activity of a target gene Inhibition may also be referred to as down-regulation or silencing of a target gene.

A siRNA or dsRNA is a double-stranded nucleic acid molecule that is capable of reducing the expression of a gene or the activity of the product of such gene to an extent sufficient to achieve a desired biological or physiological effect.

The terms "mRNA polynucleotide sequence", "mRNA sequence" and "mRNA" are used interchangeably.

As used herein, the terms "polynucleotide" and "nucleic acid" may be used interchangeably and refer to nucleotide sequences comprising deoxyribonucleic acid (DNA), and ribonucleic acid (RNA). The terms are to be understood to include, as equivalents, analogs of either RNA or DNA made from nucleotide analogs. Throughout this application, mRNA sequences are set forth as representing the corresponding genes.

"Oligonucleotide" or "oligomer" refers to a deoxyribonucleotide or ribonucleotide sequence from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide. The conjugates of the present invention encompass molecules comprising deoxyribonucleotides, ribonucleotides, modified deoxyribonucleotides, modified ribonucleotides and combinations thereof.

"Nucleotide" is the monomeric unit of a nucleic acid consisting of a ribose sugar moiety (ribonucleotides) or deoxyribose sugar moiety (deoxyribonucleotides), a phosphate and a base ((adenine, guanine, thymine, or cytosine in DNA; adenine, guanine, uracil, or cytosine in RNA). The nucleotide may be natural, synthetic, modified or unmodified. Modifications include changes to the sugar moiety, the base moiety and or the linkages between ribonucleotides in the oligoribonucleotide. As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide.

The term "Substantially complementary" refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

The term "off-target" and the phrase "off-target effects" as used herein refer to any instance in which an siRNA, dsRNA or shRNA directed against a given target causes an unintended effect by interacting either directly or indirectly with another mRNA sequence, a DNA sequence, a cellular protein, or other moiety. For example, an "off-target effect" may occur when there is a simultaneous degradation of other transcripts due to partial homology or complementarity between that other transcript and the sense and/or antisense strand of the dsRNA, siRNA or shRNA.

The term "silencing" as used herein refers to RNAi (e.g. dsRNA, siRNA) mediated reduction in gene expression that can be measured by any number of methods including PCR-based methods, Northern blot analysis, western blot analysis, and other art recognized techniques.

As used herein, "linker", "linking moiety" or "linking group" refer to one or more atoms that connect one chemical moiety to another chemical moiety.

The linker may be a nucleotide or non-nucleotide agent comprising at least one atom including carbon, oxygen, sulfur, nitrogen and phosphorus atoms or combinations thereof. According to some embodiments, the linker comprises substituted or unsubstituted, branched, unbranched or cyclic hydrocarbyl groups of up to 30 carbon atoms optionally interrupted by up to 10 heteroatoms or a peptidy chain of up to 20 amino acid residue. According to some embodiments, linkers comprise low molecular weight groups such as amide, ester, carbonate and ether, as well as higher molecular weight linking groups such as alkane-diol based linkers such as butanediol, polyethylene glycol (PEG) based linkers having between 2 and 100 ethylene glycol units, such as for example triethylene glycol units or hexaethylene glycol units, abasic linkers (dSpacers), a peptide, a lipid, a nucleic acid and. As disclosed herein, having a "linker" refers to a molecule that connects the moiety of figure (I) to a nucleic acid molecule. According to some embodiments, several linking groups covalently attached to each other, may be used to connect the moiety of formula (I) to the nucleic acid molecule. If more than one linker or linking unit is involved, the linker units may be linked to each other via phosphodiester, phosphorothioate, methylphosphonate, or amide linkages.

According to some embodiments, the linker may be independently selected from the group consisting of a carbon linker, a linker comprising a sugar moiety, a peptide linker, a nucleotide linker, an amido alkyl linker, a phosphodiester linker and a phosphorothioate linker.

According to certain embodiments, the linker comprises two functional groups or atoms: one end of the linker includes one functional group or atoms for covalent binding to a nucleotide in the sense strand and/or antisense strand and one end of the linker includes one functional group or atoms for covalent binding the first linker to the phenyl hydrocarbyl moiety or the second linker to the delivery agent. In some embodiments, the linker is a substituted or unsubstituted alkane or alkene, for example a substituted or unsubstituted ethane, ethylene, propane, propylene, butane, butylene, pentane, pentene, hexane, hexene, heptane, heptene, octane, octene, nonane, nonene, dodecane or dodecene. In some embodiments, the linker includes a linking group such as a $C_1$-$C_{24}$ alkyl linker. In some embodiments, linker is a $C_2$-$C_{30}$ alkyl linker. In some embodiments, the linker is a $C_3$-$C_{24}$, $C_3$-$C_{18}$, $C_6$-$C_{18}$, $C_6$-$C_{12}$ linker or a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$ or a $C_{24}$ alkyl linker. In various embodiments, the linker includes an amino, amido group or thiol group. For example, the linker may include alkylamino linkers, such as $C_3$, $C_6$, $C_{12}$ aminolinkers, and also alkylthiol linkers, such as $C_3$ or $C_6$ thiol linkers. According to some embodiments, the linker may have the structure [($CH_2$)a-Pi-($CH_2$)b]c wherein a and b are independently an integer from 1-6 and c is an integer from 1-12; A "Pi" refers to an inorganic phosphate and includes for example, phosphodiester and phosphorothioate.

According to some embodiments, more than one moiety of formula (I), alternatively more than 2 moieties of formula (I), alternatively, three moieties of formula (I) may be attached to any one of the terminal nucleotides of the dsRNA of the invention through the use of a "comb-like" linkers (alternatively refer to as "fork-like" linkers), such as for example linkers comprising a doubler or trebler moieties, some of which are commercially available. According to some embodiments, the doubles or trebler units may be symmetric or asymmetric.

According to some embodiments, the linker is a nucleotide linker. A nucleotide linker can be a linker of ≥2 nucleotides in length, for example about 3, 4, 5, 6, 7, 8, 9, or 10 nucleotides in length.

Specific examples for linkers that may be used in compounds and compositions of the invention include those described by Seela and Kaiser, Nucleic Acids Res. 1990, 18:6353 and Nucleic Acids Res. 1987, 15:3113; Cload and Schepartz, J. Am. Chem. Soc. 1991, 113:6324; Richardson and Schepartz, J. Am. Chem. Soc. 1991, 113:5109; Ma et al., Nucleic Acids Res. 1993, 21:2585 and Biochemistry 1993, 32:1751; Durand et al., Nucleic Acids Res. 1990, 18:6353; McCurdy et al., Nucleosides & Nucleotides 1991, 10:287; Jschke et al., Tetrahedron Lett. 1993, 34:301; Ono et al., Biochemistry 1991, 30:9914; Arnold et al., International Publication No. WO 89/02439; Usman et al., International Publication No. WO 95/06731; Dudycz et al., International Publication No. WO 95/11910 and Ferentz and Verdine, J. Am. Chem. Soc. 1991, 113:4000.

The linkage between the oligonucleotide and the lipophilic residue may be a metabolically stable or metabolically labile one.

According to some embodiments, the moiety of formula (I) may be covalently connected to any terminal nucleotide of the dsRNA of the invention through any known in the art linker capable of linking to an oligonucleotide, for example a linker comprising phosphodiester, phosphorothioate, methylphosphonate, amide linkages and the like.

Chemical Definitions

The term "hydrocarbyl", "hydrocarbyl groups" or "hydrocarbyl moiety" in compounds and conjugates of the invention refer to the residues of hydrocarbon groups, that is, hydrocarbon chain radicals, that may be unsaturated or saturated, linear, branched, cyclic, or aromatic, preferably independently selected from alkyl, alkenyl, alkynyl, aryl and aralkyl. Non-limiting examples of hydrocarbyl groups include ($C_1$-$C_8$)alkyl, ($C_2$-$C_8$)alkenyl, ($C_2$-$C_8$)alkynyl, ($C_3$-$C_{10}$)cycloalkyl, ($C_3$-$C_{10}$)cycloalkenyl, ($C_6$-$C_{10}$)aryl, ($C_1$-$C_8$)alkyl($C_6$-$C_{10}$)aryl, and ($C_6$-$C_{10}$)aryl($C_1$-$C_8$)alkyl.

The term "phenyl hydrocarby", "phenyl hydrocarbyl group" or "phenyl hydrocarbyl moiety" as used herein refers specifically to hydrocarbyl group, which comprises a phenyl group. The phenyl group may be substituted or unsubstituted.

The term "alkyl" as used herein alone or as part of another group denotes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term $C_1$-$C_{12}$ includes alkyl groups containing 1 to 12 carbon atoms. The alkyl group may be unsubstituted, or substituted with one or more substituents selected from the group consisting of halogen, hydroxyl, alkoxy, aryloxy, alkylaryloxy, heteroaryloxy, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, oxo, cycloalkyl, phenyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkoxy" as used herein alone or as part of another group refers to substituted and unsubstituted alkyl, alkenyl, and alkynyl groups covalently linked to an oxygen atom. Examples of alkoxy groups include methoxy, ethoxy, isopropyloxy, propoxy, butoxy, pentoxy and hexoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "halogen" or "halo" as used herein refers to fluorine, chlorine, bromine, and iodine.

The term "phosphate moiety" as used herein refers to a monophosphate moiety of the general formula —[O—P(O)($R^8$)—O]$^{2-}$, a diphosphate moiety of the general formula —[O—P(O)($R^8$)—O—P(O)($R^8$)—O]$^{3-}$, or a triphosphate moiety of the general formula —[O—P(O)($R^8$)—O—P(O)($R^8$)—O—P(O)($R^8$)—O]$^{4-}$, wherein $R^8$ each independently is O$^-$, S$^-$, BH$_3^-$, CH$_3$ or NR$_2$, preferably to such mono-, di- and tri-phosphate moieties wherein (i) each $R^8$ is O$^-$; or (ii) one of the $R^8$, preferably the $R^8$ linked to the phosphate atom at position α, is S$^-$, BH$_3^-$, NR$_2$ or CH$_3$ and the other $R^8$ are O$^-$, as well as to any protonated form thereof. Preferred are monophosphate moieties as defined above, such as —[O—PO$_3$]$^{2-}$, —[O—PO$_2$S]$^{2-}$, and —[O—PO$_2$(BH$_3$)]$^{2-}$, more preferably —[O—PO$_3$]$^{2-}$. As used herein R is independently selected from H and a $C_1$-$C_4$ hydrocarbyl group.

Nucleobases

Nucleobases of the nucleic acid disclosed herein may include unmodified ribonucleotides (purines and pyrimidines) such as adenine, guanine, cytosine, uracil which are the most common bases found in RNA.

The nucleobases in one or both strands can be modified or replaced to provide an RNA compound having improved properties, e.g., nuclease resistance and include natural and synthetic nucleobases such as, thymine, xanthine, hypoxanthine, nebularine, isoguanosine, inosine, 2-aminoadenine, 6-methyl and other alkyl derivatives of adenine and guanine, any "unusual bases" and "universal base" nucleotides; 2-propyl, 2-aminoadenine, 6-methyl and other alkyl derivatives of adenine and guanine, 5-halouracil and cytosine, 5-propynyl uracil and cytosine, 6-azo uracil, cytosine and thymine, 5-uracil (pseudouracil), 5-halouracil, 5-(2-aminopropyl)uracil, 5-amino allyl uracil, 4-thiouracil, 8-halo, amino, thiol, thioalkyl, hydroxyl and other 8-substituted adenines and guanines, 5-trifluoromethyl and other 5-substituted uracils and cytosines, 7-alkylguanine, 7-methylguanine, deazapurines, heterocyclic substituted analogs of purines and pyrimidines, e.g., aminoethyoxy phenoxazine, derivatives of purines and pyrimidines (e.g., 1-alkyl-, 1-alkenyl, heteroaromatic- and 1-alkynyl derivatives) and tautomers thereof, 8-oxo-N6-methyladenine, 7-diazaxanthine, 5-methylcytosine, 5-methyluracil, 5-(1-propynyl)uracil, 5-(1-propynyl) cytosine and 4,4-ethanocytosine), 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 5-alkyl cytosine, 7-deazaadenine, $N^6$-dimethyladenine, 2,6-diaminopurine, 5-amino-allyl-uracil, $N^3$-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, $N^4$-acetyl cytosine, 2-thiocytosine, $N^6$-methyladenine, $N^6$-isopentyladenine, 2-methylthio-$N^6$-isopentenyladenine, N-methylguanines, or O-alkylated bases. Other examples of suitable bases include non-purinyl and non-pyrimidinyl bases such as 2-aminopyridine and triazines.

Sugar Moieties

Sugar moieties in nucleic acid disclosed herein may include 2'-hydroxyl-pentofuranosyl sugar moiety. The 2'-hydroxyl-pentofuranosyl sugar moiety may be modified or unmodified. According to some embodiments, the 2'-hydroxyl-pentofuranosyl sugar moiety is unmodified. Alternatively, sugar moieties can be modified such as, 2'-deoxypentofuranosyl sugar moiety, D-ribose, hexose, modification at the 2' position of the pentofuranosyl sugar moiety such as 2'-O-alkyl (including 2'-O-methyl and 2'-O-ethyl), i.e., 2'-alkoxy, 2'-amino, 2'-O-allyl, 2'-S-alkyl, 2'-halogen (including 2'-fluoro, chloro, and bromo), 2'-methoxyethoxy, 2'-O-methoxyethyl, 2'-O-2-methoxyethyl, 2'-allyloxy (OCH2CH=CH2), 2'-propargyl, 2'-propyl, ethynyl, ethenyl, propenyl, CF, cyano, imidazole, carboxylate, thioate, C1 to C10 lower alkyl, substituted lower alkyl, alkaryl or aralkyl, OCF3, OCN, O-, S-, or N-alkyl; O-, S, or N-alkenyl; SOCH3; SO2CH3; ONO2; NO2, N3; heterozycloalkyl; heterozycloalkaryl; aminoalkylamino; polyalkylamino or substituted silyl, as, among others, for example as described in European patents EP 0 586 520 B1 or EP 0 618 925 B1.

Backbone

The nucleoside subunits of the nucleic acid disclosed herein may be linked to each other by phosphodiester bond. The phosphodiester bond may be optionally substituted with other linkages. For example, phosphorothioate, thiophosphate-D-ribose entities, triester, thioate, 2'-5' bridged backbone (may also be referred to as 5'-2' or 2',5' nucleotide or 2',5' ribonucleotide or 2',5' linked nucleotide or 2',5' linked ribonucleotide), PACE, 3'-(or -5')deoxy-3'-(or -5')thio-phosphorothioate, phosphorodithioate, phosphoroselenates, 3'-(or -5')deoxy phosphinates, borano phosphates, 3'-(or -5') deoxy-3'-(or 5'-)amino phosphoramidates, hydrogen phosphonates, phosphonates, borano phosphate esters, phosphoramidates, alkyl or aryl phosphonates and phosphotriester modifications such as alkylphosphotriesters, phosphotriester phosphorus linkages, 5'-ethoxyphosphodiester, P-alkyloxyphosphotriester, methylphosphonate, and non-phosphorus containing linkages for example, carbonate, carbamate, silyl, sulfur, sulfonate, sulfonamide, formacetal, thioformacetal, oxime, methyleneimino, methylenemethylimino, methylenehydrazo, methylenedimethylhydrazo and methyleneoxymethylimino linkages.

Nucleic acid molecules disclosed herein may include a peptide nucleic acid (PNA) backbone. The PNA backbone includes repeating N-(2-aminoethyl)-glycine units linked by peptide bonds. Nucleic acid bases as defined above including purine, pyrimidine, natural and synthetic bases may be linked to the PNA backbone by methylene carbonyl bonds.

Terminal Phosphates

The siRNA or dsRNA compounds of the invention may be further modified at their terminal phosphate groups.

Modifications can be made at terminal phosphate groups. Non-limiting examples of different stabilization chemistries can be used, e.g., to stabilize the 3'-end of nucleic acid sequences, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. In addition, unmodified backbone chemistries can be combined with one or more different backbone modifications described herein. Non-limiting examples of chemically modified terminal phosphate groups include those shown below:

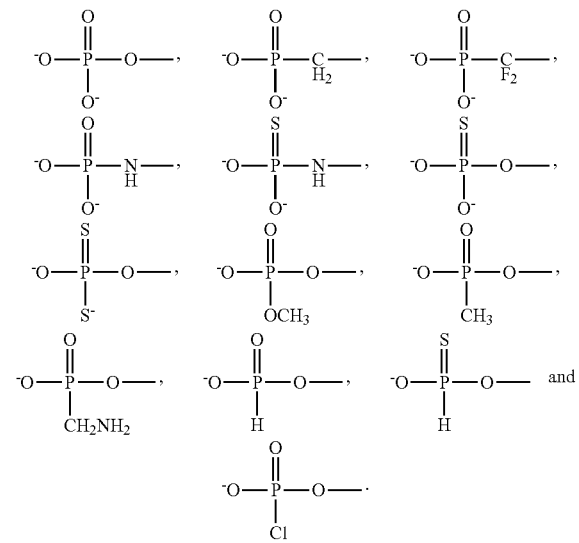

Terminal Non-Nucleotide Moieties

In some embodiments the nucleic acid molecule includes one or more 3' terminal non-nucleotide moieties covalently attached to the 3' terminus. Each such moiety may independently include an alkyl moiety, optionally propane [(CH2)$_3$] moiety (C$_3$) or a derivative thereof including propanol (C$_3$—OH) and phospho derivative of propanediol ("C$_3$-3'Pi"). In some embodiments alkyl moieties are covalently linked to the 3' terminus of the antisense strand or sense strand via a phosphodiester or phosphorothioate linkage and covalently linked to one another via a phosphodiester or phosphorothioate linkage and in some examples is C$_3$Pi-C$_3$Pi or C$_3$Pi-C$_3$OH. The 3' terminus of the antisense strand and/or the 3' terminus of the sense strand is covalently attached to a C$_3$ moiety via a phospho-based bond and the C$_3$ moiety is covalently conjugated a C$_3$—OH moiety via a phospho-based bond. In some embodiments the phospho-based bonds include a phosphorothioate, a phosphonoacetate or a phosphodiester bond. In preferred embodiments the phospho-based bond includes a phosphodiester bond.

In various embodiments the conjugate includes a retinoid covalently attached to the 5' terminus of the sense strand and has no 3' terminal moieties. In other embodiments the conjugate includes a retinoid covalently attached to the 5' terminus of the sense strand and at least one 3' terminal non-nucleotide moiety is present on the sense strand, on the antisense strand or on both the sense and antisense strands. In some embodiments each of the terminal non-nucleotide moiety includes a C$_2$, C$_3$, C$_4$, C$_5$ or C$_6$ alkyl moiety, optionally a C$_3$ [propane, —(CH$_2$)$_3$—] moiety or a derivative thereof including propanol (C$_3$—OH/C$_3$OH), propanediol, and phosphodiester derivative of propanediol ("C$_3$Pi"). In preferred embodiments the terminal moiety includes two hydrocarbon moieties and in some examples is C$_3$Pi-C$_3$OH or C$_3$Pi-C$_3$Pi. Each C$_3$ is covalently conjugated to an adjacent C$_3$ via a covalent bond, preferably a phospho-based bond. In some embodiments the phospho-based bond is a phosphorothioate, a phosphonoacetate or a phosphodiester bond.

In specific embodiments each of the sense strand and antisense strand comprises at least one 3' terminal $C_3$ alkyl overhang. In some embodiments the $C_3$-$C_3$ overhang is covalently attached to the 3' terminus of (N)x or (N')y via a covalent linkage, preferably a phosphodiester linkage. In some embodiments the linkage between a first $C_3$ and a second $C_3$ is a phosphodiester linkage. In some embodiments the 3' non-nucleotide overhang is $C_3$Pi-C3Pi. In some embodiments the 3' non-nucleotide overhang is $C_3$Pi-$C_3$Ps. In some embodiments the 3' non-nucleotide overhang is $C_3$Pi-$C_3$OH (OH is hydroxy). In some embodiments the 3' non-nucleotide overhang is $C_3$Pi-$C_3$OH.

In various embodiments the alkyl moiety comprises an alkyl derivative including a $C_3$ alkyl, $C_4$ alkyl, $C_5$ alky or $C_6$ alkyl moiety comprising a terminal hydroxyl, a terminal amino, or terminal phosphate group. In some embodiments the alkyl moiety is a $C_3$ alkyl or $C_3$ alkyl derivative moiety. In some embodiments the $C_3$ alkyl moiety comprises propanol, propylphosphate, propylphosphorothioate or a combination thereof. The $C_3$ alkyl moiety is covalently linked to the 3' terminus of (N')y and/or the 3' terminus of (N)x via a phosphodiester bond. In some embodiments the alkyl moiety comprises propanol, propyl phosphate or propyl phosphorothioate. In some embodiments a 3' terminal non-nucleotide is selected from propyl phosphate, propyl phosphorothioate, propyl phospho-propanol; propyl phospho-propyl phosphorothioate; propylphospho-propyl phosphate; (propyl phosphate)3, (propyl phosphate)2-propanol, (propyl phosphate)2-propyl phosphorothioate. Non-limiting exemplary 3' terminal non-nucleotide moieties are as follows:

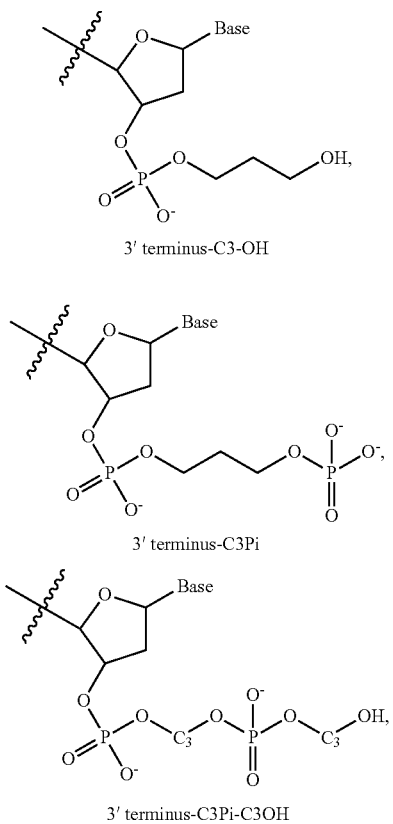

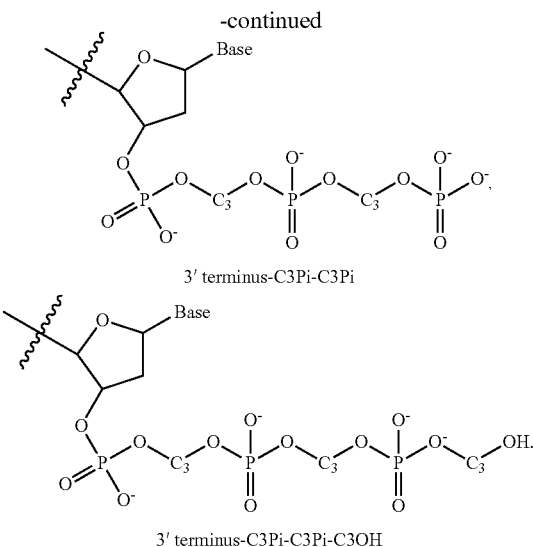

Modifications

According to some embodiments, at least one nucleotide of the sense strand or of the antisense strand comprises a modified nucleotide. The modification may comprise, for example, a sugar modification, a base modification or an internucleotide linkage modification, and may contain modified nucleotides such as LNA (locked nucleic acid) including ENA (ethylene-bridged nucleic acid); PNA (peptide nucleic acid); arabinoside; PACE (such as phosphonoacetate, phosphonocarboxylate or phosphinocarboxylate nucleotides and derivatives thereof), or nucleotides with a six-carbon sugar or an unconventional moiety selected from an abasic ribose moiety, an abasic deoxyribose moiety, a modified or unmodified deoxyribonucleotide, a mirror nucleotide, and a nucleotide joined to an adjacent nucleotide by a 2'-5' internucleotide phosphate bond. According to some embodiments the modified siRNA compound comprises at least one ribonucleotide comprising a 2' modification on the sugar moiety ("2' sugar modification"). In certain embodiments the compound comprises 2'O-alkyl or 2'-fluoro or 2'O-allyl or any other 2' modification, optionally on alternate positions. Other stabilizing modifications are also possible (e.g. terminal modifications). In some embodiments a preferred 2'O-alkyl is 2'O-methyl(methoxy) sugar modification. In some embodiments a modified ribonucleotide is a 2' OMe sugar modified ribonucleotide.

In some embodiments, the pentafuronosyl ring may be replaced with acyclic derivatives lacking the C2'-C3'-bond of the pentafuronosyl ring. For example, acyclonucleotides may substitute a 2-hydroxyethoxymethyl group for-the 2'-deoxyribofuranosyl sugar normally present in dNMPs.

All analogs of, or modifications to, a nucleotide/oligonucleotide are employed with the present invention, provided that said analog or modification does not substantially adversely affect the properties, e.g. function, of the nucleotide/oligonucleotide. Acceptable modifications include modifications of the sugar moiety, modifications of the base moiety, modifications in the internucleotide linkages and combinations thereof.

As used herein, the terms "non-pairing nucleotide analog" means a nucleotide analog which comprises a non-base pairing moiety including but not limited to: Purine 9β-D-ribofuranoside (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide. In addition, analogs of polynucleotides may be prepared wherein the structure of one or more nucleotide is fundamentally altered and better suited as therapeutic or experimental reagents. An example of a nucleotide analog is a peptide nucleic acid (PNA) wherein the deoxyribose (or ribose) phosphate backbone in DNA (or RNA is replaced with a polyamide backbone which is similar to that found in peptides. Other modifications include polymer backbones, cyclic backbones, acyclic backbones, thiophosphate-D-ribose backbones, triester backbones, thioate backbones, 2'-5' bridged backbone, artificial nucleic acids, morpholino nucleic acids, glycol nucleic acid (GNA), threose nucleic acid (TNA), arabinoside, and mirror nucleoside (for example, beta-L-deoxyribonucleoside instead of beta-D-deoxyribonucleoside). Examples of siRNA compounds comprising LNA nucleotides are disclosed in Elmen et al., (NAR 2005, 33(1):439-447).

In some embodiments the conjugates disclosed herein are synthesized with one or more inverted nucleotides, for example inverted thymidine or inverted adenine (see, for example, Takei, et al., 2002, JBC 277(26):23800-06). Other modifications include 3' terminal modifications also known as capping moieties. Such terminal modifications are selected from a nucleotide, a modified nucleotide, a lipid, a peptide, a sugar and inverted abasic moiety. Such modifications are incorporated, for example at the 3' terminus of the sense and/or antisense strands.

"Abasic nucleotide" or "abasic nucleotide analog" also referred to a pseudo-nucleotide or an unconventional moiety refers to a nucleotide lacking a base.

The term "capping moiety" as used herein may include without limitation, unmodified or modified abasic ribose moiety, unmodified or modified abasic deoxyribose moiety (modification may include for example 2' O alkyl modifications); inverted abasic ribose and abasic deoxyribose moieties and modifications thereof; C6-imino-Pi; a mirror nucleotide including L-DNA and L-RNA; 5'O-Me nucleotide and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties. Certain preferred capping moieties are abasic ribose or abasic deoxyribose moieties; inverted abasic ribose or abasic deoxyribose moieties; C6-amino-Pi; a mirror nucleotide including L-DNA and L-RNA. As used herein, the moiety of formula (I) covalently attached directly or via a linker to the 3' or 5' termini of a sense and/or antisense strands of the dsRNA may be also referred to as a capping moiety.

The term "unconventional moiety" as used herein refers to abasic ribose moiety, an abasic deoxyribose moiety, a deoxyribonucleotide, a modified deoxyribonucleotide, a mirror nucleotide, a non-base pairing nucleotide analog and a nucleotide joined to an adjacent nucleotide by a 2'-5' internucleotide phosphate bond; (2'5' nucleotide which may comprise for example 3'H, 3'OH or 3'-O-Me on the sugar residue) bridged nucleic acids including locked nucleic acids (LNA) and ethylene bridged nucleic acids (ENA).

Abasic deoxyribose moiety includes for example abasic deoxyribose-3'-phosphate; 1,2-dideoxy-D-ribofuranose-3-phosphate; 1,4-anhydro-2-deoxy-D-ribitol-3-phosphate. Inverted abasic deoxyribose moiety includes inverted deoxyriboabasic; 3',5' inverted deoxyabasic 5'-phosphate.

A "mirror" nucleotide is a nucleotide with reversed chirality to the naturally occurring or commonly employed nucleotide, i.e., a mirror image (L-nucleotide) of the naturally occurring (D-nucleotide), also referred to as L-RNA in the case of a mirror ribonucleotide, and "spiegelmer". The nucleotide can be a ribonucleotide or a deoxyribonucleotide and may further comprise at least one sugar, base and or backbone modification. Mirror nucleotide includes for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror dT) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

Modified deoxyribonucleotide includes, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate).

Bridged nucleic acids include LNA (2'-O, 4'-C-methylene bridged Nucleic Acid adenosine 3' monophosphate, 2'-O,4'-C-methylene bridged Nucleic Acid 5-methyl-cytidine 3' monophosphate, 2'-O,4'-C-methylene bridged Nucleic Acid guanosine 3' monophosphate, 5-methyl-uridine (or thymidine) 3' monophosphate); and ENA (2'-O,4'-C-ethylene bridged Nucleic Acid adenosine 3' monophosphate, 2'-O,4'-C-ethylene bridged Nucleic Acid 5-methyl-cytidine 3' monophosphate, 2'-O,4'-C-ethylene bridged Nucleic Acid guanosine 3' monophosphate, 5-methyl-uridine (or thymidine) 3' monophosphate).

dsRNA Structure

In various embodiments provided herein, the structure of the conjugate is as set forth in structure (A) below:

(A) 5'  (N)$_x$-Z  3'  (antisense strand)

3'  Z'-(N')$_y$-z"  5'  (sense strand)

wherein each of N and N' is a ribonucleotide which may be unmodified or modified, or an unconventional moiety;

wherein each of (N)x and (N')y is an oligoribonucleotide in which each consecutive N or N' is joined to the next N or N' by a covalent bond;

wherein each of x and y is independently an integer between 15 and 40;

wherein at least one of Z, Z' and z" is present and is a moiety of formula (I) covalently attached directly or via a linker to the terminus of the strand in which it is present; wherein:

(a) if z" is present, each of Z and Z' is independently present or absent, but if present comprises independently a moiety of formula (I), a delivery moiety or 1-5 consecutive nucleotides, consecutive non-nucleotide moieties or a combination thereof covalently attached at the 3' terminus of the strand in which it is present; or (b) if at least one of Z or Z' is present, z" may be present or absent, but if present comprises a moiety of formula (I), a delivery moiety or a capping moiety covalently attached at the 5' terminus of the sense strand, and wherein the remaining Z or Z' is present or absent, but if present independently comprises a moiety of formula (I), a delivery moiety or 1-5 consecutive nucleotides, consecutive non-nucleotide moieties or a combination thereof covalently attached at the 3' terminus of the strand in which it is present; and wherein the sequence of (N')y is complementary to the sequence of (N)x; and wherein (N)x comprises an antisense that is complementary to about 15 to about 40 consecutive nucleotides in a target RNA.

According to some embodiments, the sequence of (N')y is fully complementary to the sequence of (N)x.

According to some embodiments, the sequence of (N')y is partially complementary to the sequence of (N)x and includes at least one mismatch between the sequence of (N')y and the sequence of (N)x. According to some embodiments, at least two mismatches between the sequence of (N')y and the sequence of (N)x; alternatively, at least 3 mismatches between the sequence of (N')y and the sequence of (N)x.

In some embodiments the sequence of the sense strand (N')y has sequence identity to a segment of a mRNA corresponding to a target gene. According to some embodiments, the sequence of (N')y is fully identical to the sequence of the a segment of a mRNA corresponding to a target gene. According to some embodiments, each of the sense strands and the antisense strand is independently 18-40 nucleotides in length, preferably 18 to 25 ribonucleotides, more preferably 19 to 23 ribonucleotides. In some embodiments the length of each strand (oligomer) is independently selected from the group consisting of about 18 to about 40 bases, preferably 18 to 23 bases and more preferably 19, 20 or 21 ribonucleotides. In some embodiments, the length is 19 bases.

In some embodiments the double-stranded nucleic acid molecule includes a phenyl hydrocarbon moiety (PHM) covalently linked to the 5' terminus of the sense strand has the structure:

attached form a C6 cycloalkyl ring, $R^3$ is C3 and X is O), and said moiety of formula (I) comprising a THNB moiety is covalently attached to the 5' terminus of the sense strand. As used herein, the THNB comprising moiety covalently attached to the 5' terminus of a sense strand may be also known as a capping moiety. According to some embodiments the dsRNA is blunt ended at the 3' terminus of the compound, i.e. 3' terminus of (N')y and 5' terminus of (N)x. More specifically, the dsRNA is blunt ended on the end defined by the 3'-terminus of the (N')y and the 5'-terminus of (N)x.

According to some embodiments the dsRNA comprising an assymetric dsRNA molecule, for example as described by Chu and Rana (RNA. 2008, 14(9):1714-9).

According to some embodiments at least one of the two strands has an overhang (Z or Z') comprising at least one nucleotide at the 3'-terminus; the overhang comprises at least one deoxyribonucleotide. At least one of the strands optionally comprises an overhang of at least one nucleotide at the 3'-terminus. The overhang consists of from about 1 to about 5 nucleotides or non-nucleotides.

Unless otherwise indicated, in preferred embodiments the covalent bond between each consecutive ribonucleotide in an oligonucleotide strand is a phosphodiester bond. In some embodiments at least one covalent bond is a phosphorothioate bond.

According to some embodiments the double-stranded nucleic acid molecule of the invention comprises an antisense strand comprising a mirror nucleotide or a 2'-5' linked ribonucleotide in one or more of positions 5, 6, 7 or 8 (5'-3'), and a nucleotide or non-nucleotide moiety covalently attached at the 3' terminus. According to some embodiments the antisense strand further comprises one or more 2'OMe sugar modified ribonucleotides. According to some embodiments 1, 2, 3, 4, 5, 6, 7, 8 or 9 pyrimidine ribonucleotides in the antisense strand are 2'OMe sugar modified pyrimidine ribonucleotides. According to some embodiments the sense strand includes 4 or 5 consecutive 2'-5' linked nucleotides at the 3' terminal or penultimate positions, a nucleotide or

wherein each "|" represents base pairing between the ribonucleotides;

wherein each N or N' is any one of A, C, G, U and is independently an unmodified or modified ribonucleotide, or is an unconventional moiety;

wherein z" is a moiety of formula (I) covalently attached at the 5' terminus of the sense strand; and wherein each of Z and Z' is independently present or absent, but if present is independently a delivery agent, a moiety of formula (I) or 1-5 consecutive nucleotides or non-nucleotide moieties or a combination thereof covalently attached at the 3' terminus of the strand in which it is present.

According to some embodiments the double-stranded nucleic acid molecule comprises a 19-mer antisense strand, a complementary 19-mer sense strand to generate a 19-mer duplex. According to some embodiments, each of the ribonucleotides in the sense or antisense strands may be an unmodified ribonucleotide, a modified ribonucleotide may comprise an unconventional moiety.

In preferred embodiments the moiety of formula (I) comprises THNB moiety (the moiety of formula (I) wherein $R^1$ and $R^2$ together with the carbon to which they are non-nucleotide moiety covalently attached at the 3' terminus, one or more 2'OMe sugar modified ribonucleotides, and a molecule comprising a moiety represented by the general formula (I) is covalently attached at the 5' terminus directly or via a linker. The dsRNA molecule may include a 5' phosphate on the antisense strand. Each possibility described above represents a separate embodiment of the invention. According to some embodiments the double-stranded nucleic acid molecule of the invention comprises an antisense strand which includes (5'>3') 1, 2, 3, 4, 5, 6, 7, 8 or 9 2'OMe sugar modified pyrimidine ribonucleotides, and a $C_3Pi-C_3OH$ moiety covalently attached to the 3' terminus; and a sense strand which includes (5'>3') 2'-5' linked ribonucleotides at positions 15, 16, 17, 18 and 19, a 3' terminal nucleotide or non-nucleotide overhang; and a molecule comprising a phenyl hydrocarbyl moiety represented by the general formula (I) covalently attached at the 5' terminus directly or via a linker. In some embodiments the antisense strand further comprises a 2'-5' linked ribonucleotide at position 6, at position 7 or at positions 6 and 7.

According to some embodiments the double-stranded nucleic acid molecule comprises an antisense strand which includes (5'>3') 1, 2, 3, 4, 5, 6, 7, 8 or 9 2'OMe sugar modified pyrimidine ribonucleotides, and a $C_3Pi-C_3OH$ moiety covalently attached to the 3' terminus; and a sense strand which includes (5'>3') 2'-5' linked ribonucleotides at positions 15, 16, 17, 18 and 19, a $C_3Pi$ or $C_3OH$ moiety covalently attached to the 3' terminus; and a molecule comprising a phenyl hydrocarbyl moiety represented by the general formula (I) covalently attached at the 5' terminus directly or via a linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, and a $C_3Pi-C_3OH$ moiety covalently attached to the 3' terminus; and the sense strand includes (5'>3') 2'-5' linked ribonucleotides at positions 15, 16, 17, 18 and 19, a $C_3Pi$ covalently attached to the 3 terminus and a molecule comprising a moiety represented by the general formula (I) covalently attached at the 5' terminus directly or via a linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, a 2'-5' linked ribonucleotide or a mirror nucleotide in one or more of positions 6, 7 and 8, and a $C_3Pi-C_3OH$ moiety covalently attached to the 3' terminus; and a sense strand comprising (5'>3') 2'-5' linked ribonucleotides at positions 15, 16, 17, 18 and 19, a 3' terminal nucleotide or non-nucleotide overhang; and a molecule comprising a phenyl hydrocarbyl moiety represented by the general formula (I) covalently attached at the 5' terminus directly or via a linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, a 2'-5' linked ribonucleotide at position 6, and a $C_3Pi-C_3OH$ moiety covalently attached to the 3' terminus; and a sense strand comprising (5'>3') 2'-5' linked ribonucleotides at positions 15, 16, 17, 18 and 19, a $C_3Pi$ or $C_3OH$ moiety covalently attached to the 3' terminus; and a molecule comprising a moiety represented by the general formula (I) covalently attached at the 5' terminus directly or via a linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, a 2'-5' linked ribonucleotide at position 6, and a $C_3Pi-C_3OH$ moiety covalently attached to the 3' terminus; and a sense strand comprising (5'>3') 2'-5' linked ribonucleotides at positions 15, 16, 17, 18 and 19, a $C_3Pi$ covalently attached to the 3 terminus and a molecule comprising a moiety represented by the general formula (I) covalently attached at the 5' terminus directly or via a linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, a 2'-5' linked ribonucleotide at position 6, and a $C_3Pi-C_3OH$ moiety covalently attached to the 3' terminus; and a sense strand comprising (5'>3') 2'-5' linked ribonucleotides at positions 15, 16, 17, 18 and 19, a $C_3Pi$ covalently attached to the 3 terminus; and a molecule comprising a moiety represented by the general formula (I) covalently attached at the 5' terminus directly or via a linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, a 2'-5' linked ribonucleotide at position 7, and a $C_3Pi-C_3OH$ moiety covalently attached to the 3' terminus; and a sense strand comprising (5'>3') a 2'OMe sugar modified ribonucleotide at position 1, 2'-5' linked ribonucleotides at positions 15, 16, 17, 18 and 19, a $C_3Pi$ or $C_3OH$ moiety covalently attached to the 3' terminus; and a molecule comprising a moiety represented by the general formula (I) covalently attached at the 5' terminus directly or via linker According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, a 2'-5' linked ribonucleotide at position 7, and a $C_3Pi-C_3OH$ moiety covalently attached to the 3' terminus; and a sense strand comprising (5'>3') a 2'OMe sugar modified ribonucleotide at position 1, a $C_3Pi$ moiety covalently attached to the 3 terminus; and a molecule comprising a moiety represented by the general formula (I) covalently attached at the 5' terminus directly or via linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, a 2'-5' linked ribonucleotide at position 7, and a $C_3Pi-C_3OH$ moiety covalently attached to the 3' terminus; and a sense strand comprising (5'>3') a 2'OMe sugar modified ribonucleotide at position 1, and 2'-5' linked ribonucleotides at positions 15, 16, 17, 18 and 19, a $C_3Pi$ covalently attached to the 3 terminus; and a molecule comprising a moiety represented by the general formula (I) covalently attached at the 5' terminus directly or via a linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, 2'-5' linked ribonucleotide at positions 6 and 7 and a $C_3Pi-C_3OH$ moiety covalently attached to the 3' terminus; and a sense strand comprising (5'>3') a 2'OMe sugar modified ribonucleotide at position 1, 2'-5' linked ribonucleotides at positions 15, 16, 17, 18 and 19, a $C_3Pi$ or $C_3OH$ moiety covalently attached to the 3' terminus; and a molecule comprising a moiety represented by the general formula (I) covalently attached at the 5' terminus directly or via a linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, a 2'-5' linked ribonucleotide at positions 6 and 7 and a $C_3Pi-C_3OH$ moiety covalently attached to the 3' terminus; and a sense strand comprising (5'>3') a 2'OMe sugar modified ribonucleotide at position 1, 2'-5' linked ribonucleotides at positions 15, 16, 17, 18 and 19, a $C_3Pi$ moiety covalently attached to the 3 terminus; and a molecule comprising a moiety represented by the general formula (I) covalently attached at the 5' terminus directly or via a linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, a mirror nucleotide at position 6 and a $C_3Pi-C_3OH$ moiety covalently attached to the 3' terminus; and a sense strand comprising (5'>3') a 2'OMe sugar modified ribonucleotide at position 1, and 2'-5' linked ribonucleotides at positions 15, 16, 17, 18 and 19, a $C_3Pi$ moiety covalently attached to the 3 terminus; and a molecule comprising a moiety represented by the general formula (I) covalently attached at the 5' terminus directly or via a linker.

According to some embodiments the double-stranded nucleic acid molecule comprises an antisense strand comprising (5'>3') 1, 2, 3, 4, 5, 6, 7, 8 or 9 2'OMe sugar modified pyrimidine ribonucleotides, a mirror nucleotide at position 8 and a $C_3Pi$-$C_3OH$ moiety covalently attached to the 3' terminus; and a sense strand comprising (5'>3') a 2'OMe sugar modified ribonucleotide at position 1, 2'-5' linked ribonucleotides at positions 15, 16, 17, 18 and 19, a $C_3Pi$ moiety covalently attached to the 3 terminus; and a molecule comprising a moiety represented by the general formula (I) covalently attached at the 5' terminus directly or via a linker.

According to some embodiments the double-stranded nucleic acid molecule of the invention comprises a sense strand comprising (5'>3') a 2'OMe sugar modified ribonucleotide at position 1; 2'-5' linked ribonucleotides at positions 15, 16, 17, 18 and 19, a $C_3Pi$ moiety covalently attached to the 3 terminus; and a molecule comprising a moiety represented by the general formula (I) covalently attached at the 5' terminus directly or via a linker, and the antisense strand is selected from the group consisting of:

(1) an antisense oligonucleotide comprising (5'>3') a U to dT substitution in position 1, a 5' phosphate covalently attached to the deoxyribothymidine in position 1; 1, 2, 3, 4, 5, 6, 7, 8 or 9 2'OMe sugar modified pyrimidine ribonucleotides, a 2'-5' linked ribonucleotide at position 6 or 7 and a $C_3Pi$-$C_3OH$ moiety covalently attached to the 3' terminus;

(2) an antisense oligonucleotide comprising (5'>3') a 5' phosphate covalently attached to the uridine in position 1; 1, 2, 3, 4, 5, 6, 7, 8 or 9 2'OMe sugar modified pyrimidine ribonucleotides, a 2'-5' linked ribonucleotide at position 6 or 7 and a $C_3Pi$-$C_3OH$ moiety covalently attached to the 3' terminus;

(3) an antisense oligonucleotide comprising (5'>3') a U to $C_3$ substitution in position 1, a 5' phosphate covalently attached to the $C_3$ in position 1, 2, 3, 4, 5, 6, 7, 8 or 9 2'OMe sugar modified pyrimidine ribonucleotides, a 2'-5' linked ribonucleotide at position 6 or 7 and a $C_3Pi$-$C_3OH$ moiety covalently attached to the 3' terminus; and (4) an antisense oligonucleotide comprising (5'>3') a 5' phosphate covalently attached to the uridine in position 1; 1, 2, 3, 4, 5, 6, 7, 8 or 9 2'OMe sugar modified pyrimidine ribonucleotides, a 2'-5' linked ribonucleotide at position 6 or 7 and a $C_3Pi$-$C_3OH$ moiety covalently attached to the 3' terminus.

According to some embodiments the double-stranded nucleic acid molecule of the invention comprises a sense strand comprising (5'>3') 1, 2, 3, 4, 5, 6, 7, or 8 2'OMe sugar modified pyrimidine ribonucleotides; a $C_3Pi$ moiety covalently attached to the 3 terminus; and a molecule comprising a phenyl hydrocarbyl moiety represented by the general formula (I) covalently attached at the 5' terminus directly or via a linker, and an antisense strand selected from the group consisting of:

(1) an antisense oligonucleotide comprising (5'>3') a U to dT substitution in position 1, a 5' phosphate covalently attached to the deoxyribothymidine in position 1; 1, 2, 3, 4, 5, 6, 7, 8 or 9 2'OMe sugar modified pyrimidine ribonucleotides, a 2'-5' linked ribonucleotide at position 6 or 7 and a $C_3Pi$-$C_3OH$ moiety covalently attached to the 3' terminus;

(2) an antisense oligonucleotide comprising (5'>3') a 5' phosphate covalently attached to the uridine in position 1; 1, 2, 3, 4, 5, 6, 7, 8 or 9 2'OMe sugar modified pyrimidine ribonucleotides, a 2'-5' linked ribonucleotide at position 6 or 7 and a $C_3Pi$-$C_3OH$ moiety covalently attached to the 3' terminus;

(3) an antisense oligonucleotide comprising (5'>3') a U to $C_3$ substitution in position 1, a 5' phosphate covalently attached to the $C_3$ in position 1; 1, 2, 3, 4, 5, 6, 7, 8 or 9 2'OMe sugar modified pyrimidine ribonucleotides, a 2'-5' linked ribonucleotide at position 6 or 7 and a $C_3Pi$-$C_3OH$ moiety covalently attached to the 3' terminus; and (4) an antisense oligonucleotide comprising (5'>3') a 5' phosphate covalently attached to the uridine in position 1; 1, 2, 3, 4, 5, 6, 7, 8 or 9 2'OMe sugar modified pyrimidine ribonucleotides, a 2'-5' linked ribonucleotide at position 6 or 7 and a C3Pi-C3OH moiety covalently attached to the 3' terminus.

According to some embodiments the double stranded nucleic acid of the invention further comprises one or more of the modifications:

(a) a threose nucleic acid moiety, a 2'5' nucleotide or a mirror nucleotide in the antisense strand in at least one of positions 5, 6, 7, 8, or 9 from the 5' terminus;

(b) a threose nucleic acid moiety, a 2'5' nucleotide or a pseudoUridine in the sense strand in at least one of positions 9 or 10 from the 5' terminus;

(c) from 1-10 threose nucleic acid moieties or 2'5' nucleotides in the sense strand at the 3' terminal or penultimate positions.

Nucleic Acid and Conjugate Synthesis

Using public and proprietary algorithms the sense and antisense sequences of potential nucleic acid molecules are generated. Nucleic acid molecules according to the above specifications are prepared essentially as described herein.

The dsRNA of the present invention are synthesized by any of the methods that are well known in the art for synthesis of ribonucleic (or deoxyribonucleic) oligonucleotides. Synthesis is commonly performed in a commercially available synthesizer (available, inter alia, from Applied Biosystems). Oligonucleotide synthesis is described for example in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Ann. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et al., in IRL Press 1989 edited by Oliver R. W. A.; Kap. 7: 183-208.

Other synthetic procedures are known in the art, for example, the procedures described in Usman et al., 1987, J. Am. Chem. Soc., 109, 7845; Scaringe et al., 1990, NAR., 18, 5433; Wincott et al., 1995, NAR. 23, 2677-2684; and Wincott et al., 1997, Methods Mol. Bio., 74, 59, which make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

According to some embodiments the oligonucleotides of the present invention are synthesized separately and joined together post-synthetically, for example, by ligation (Moore et al., 1992, Science 256, 9923; Draper et al., International Patent Publication No. WO 93/23569; Shabarova et al., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the modified siRNA compounds of the present invention, two or more such sequences can be synthesized and linked together for use in the present invention.

Molecules comprising phenyl hydrocarbyl groups represented by the general formula (I) and/or delivery agents may be coupled to a nucleic acid molecule through sites present naturally in nucleotides or through a linker group. The molecule comprising a phenyl hydrocarbyl moiety, the delivery agent, or the linker group may be introduced at one of various stages of oligonucleoide synthesis. The molecule comprising a phenyl hydrocarbyl moiety and/or the delivery agent may be attached to a nucleotide before incorporation of the modified nucleotide into the oligonucleotide; during synthesis of the oliginucleotide chain; or post-synthesis. The dsRNA conjugates of the invention comprise a moiety of formula (I) and may further include one or more delivery agents covalently linked at the 5' terminus of the passenger strand, at the 3' terminus of the passenger strand, or at the 3' terminus of the guide strand. The synthesis of such a dsRNA conjugate is accomplished by any of numerous methods known in the art. In some embodiments, a phosphoramidite derivative of the moiety, preferably comprising a THNB moiety, is covalently attached to the 5' terminus of the sense (passenger) strand directly or via a nucleotide or a non-nucleotide linker. In various embodiments the sense strand bearing a phenyl hydrocarbyl moiety covalently linked at its 5' terminus and the antisense strand are synthesized separately and then are annealed to each other.

In preferred embodiments a method of synthesizing a double-stranded nucleic acid conjugated to a moiety of formula (I) comprises the following steps:

Providing a sense strand oligonucleotide, which includes a 5' terminal amino linker;

Providing a complementary antisense strand;

Providing a compound comprising the moiety of formula (I) capable of bonding the dsRNA (for example a residue of the functional group phosphoramidite such compound may be, for example, represented by formula IV);

Forming a bond between the compound comprising the moiety of formula (I) and the 5' terminal amino linker under appropriate conditions to form a sense strand oligonucleotide conjugate;

Purifying the sense strand oligonucleotide conjugate;

Annealing the sense strand oligonucleotide conjugate to the antisense strand, to generate a double-stranded nucleic acid conjugate.

Pharmaceutical Compositions

While it is possible for the conjugates of the present invention to be administered as the raw chemical, it may be preferable to present or formulate them as a pharmaceutical composition. Accordingly the present invention provides a pharmaceutical composition comprising one or more of the conjugates disclosed herein and a pharmaceutically acceptable carrier. In some embodiments the pharmaceutical composition comprises two or more conjugates disclosed herein.

Further provided is a pharmaceutical composition comprising a pharmaceutically acceptable carrier and one or more of the conjugates disclosed herein at an amount effective to inhibit or reduce expression of a target gene in a cell of a mammal, the dsRNA comprising a sequence which is substantially complementary to the sequence of the mRNA of the target gene.

In some embodiments, the dsRNA conjugates of the invention are the main active component in a pharmaceutical composition. In other embodiments the siRNA conjugates of the invention are one of the active components of a pharmaceutical composition containing two or more nucleic acid molecules.

siRNA and RNA Interference

In some embodiments the double stranded nucleic acid molecules of the invention down regulate target gene expression via RNA interference (RNAi). RNAi is a phenomenon involving double-stranded (ds) RNA-dependent gene specific posttranscriptional silencing.

RNA interference (RNAi) in mammals is mediated by small interfering RNAs (siRNAs) or microRNAs (miRNAs) The corresponding process in plants is commonly referred to as specific post-transcriptional gene silencing (PTGS) or RNA silencing and is also referred to as quelling in fungi.

A siRNA is a double-stranded RNA or modified RNA molecule which down-regulates or silences (prevents) the expression of a gene/mRNA of its endogenous (cellular) counterpart.

The molecules of the present invention offer an advantage in that they are more stable and specific than analogous non-conjugated dsRNA compounds and are useful in the preparation of pharmaceutical compositions for treatment of various diseases.

According to some embodiments of the invention, the dsRNA compounds to be conjugated with a moiety represented by the general formula (I) may be selected for example from the dsRNA structures disclosed in PCT Patent Publication Nos. WO 2008/104978, WO 2009/044392 and WO 2008/050329 to the assignee of the present invention and are hereby incorporated by reference in their entirety.

The present invention provides a method of down-regulating the expression of a target gene by at least 20%, 30%, 40% or 50%, preferably by at least 50%, 60% or 70%, more preferably by at least 75%, 80% or 90% as compared to the down-regulation of the expression of the target gene by a corresponding non-conjugated dsRNA, comprising contacting an mRNA transcript of the target gene with one or more of the conjugates disclosed herein. In various embodiments down-regulation is selected from the group comprising down-regulation of gene function, down-regulation of polypeptide and down-regulation of mRNA expression. Down-regulation of target gene expression is easily assessed by testing the conjugates in an in vitro cell based system, by a person with skill in the relevant art. According to some embodiments, the present invention discloses a method of down-regulating the expression of a target gene in a mammal by at least 20%, 30%, 40% or 50%, preferably by at least 50%, 60% or 70%, more preferably by at least 75%, 80% or 90% as compared to the down-regulation of the expression of the target gene by a corresponding non-conjugated dsRNA, the method comprising administering one or more of the dsRNA conjugates disclosed herein to the mammal. In a preferred embodiment the mammal is a human. In various embodiments the conjugate down-regulates or attenuates or inhibits the expression of a target gene, whereby the down-regulation of the expression of a target gene is selected from the group comprising down-regulation of gene function (which is examined, e.g. by an enzymatic assay or a binding assay with a known interactor of the native gene/polypeptide, inter alia), down-regulation of polypeptide product of the gene (which is examined, e.g. by Western blotting, ELISA or immuno-precipitation, inter alia) and down-regulation of mRNA expression of the gene (which is examined, e.g. by Northern blotting, quantitative RT-PCR, in-situ hybridisation or microarray hybridisation, inter alia).

Delivery

The conjugates disclosed herein are administered per se (i.e. as naked conjugates) or as pharmaceutically acceptable salt and are administered alone or as an active ingredient in combination with one or more pharmaceutically acceptable carrier, solvent, diluent, excipient, adjuvant and vehicle. In some embodiments, the conjugates of the present invention are delivered to the target tissue by direct application of the naked conjugated siRNA of the invention formulated with a carrier or a diluent.

The term "naked" refers to conjugates that are free from any delivery vehicle that acts to assist, promote or facilitate entry into the cell, including viral sequences, viral particles, liposome formulations, lipofectin or precipitating agents and the like. For example a conjugate in PBS buffer is "naked conjugate".

Pharmaceutically acceptable carriers, solvents, diluents, excipients, adjuvants and vehicles as well as implant carriers generally refer to inert, non-toxic solvents, dispersion media, coatings, antibacterial and antifungal agents, isotonic and absorption delaying agents, solid or liquid fillers, diluents or encapsulating material not reacting with the conjugates disclosed herein and compatible with pharmaceutical administration. The conjugated siRNA compounds of the invention may be prepared with carriers that will protect the compound against rapid elimination from the body, such as controlled release formulation, including implants and microencapsulated delivery systems. Biodegradable, biocompatible polymers may be used, such as ethylene vinyl acetate, polyanhydrides, polyglycolic acid, collagen, polyorthoesters and polylactic acid. For example, the conjugates disclosed herein may be formulated with polyethylenimine (PEI), with PEI derivatives, e.g. oleic and stearic acid modified derivatives of branched PEI, with chitosan or with poly(lactic-co-glycolic acid) (PLGA). The conjugated siRNA compounds of the present invention may also be incorporated into or within liposomes and microspheres.

Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many such implants, delivery systems, and modules are well known to those skilled in the art. In one specific embodiment topical and transdermal formulations are selected.

Additional formulations for improved delivery of the compounds disclosed herein can include non-formulated conjugates, conjugates further covalently bound to cholesterol, and compounds bound to targeting antibodies (Song et al., Nat Biotechnol. 2005. 23(6):709-17). Cholesterol-conjugated siRNAs (and other steroid and lipid conjugated siRNAs) can been used for delivery (see for example Soutschek et al Nature. 2004. 432:173-177; and Lorenz et al. Bioorg. Med. Chem. Lett. 2004. 14:4975-4977).

The naked conjugates or the pharmaceutical compositions comprising the conjugates disclosed herein are administered and dosed in accordance with good medical practice, taking into account the clinical condition of the individual patient, the disease to be treated, the site and method of administration, scheduling of administration, patient age, sex, body weight and other factors known to medical practitioners.

A "therapeutically effective dose" for purposes herein is determined by considerations as are known in the art. The dose must be effective to achieve improvement including but not limited to improved survival rate or more rapid recovery, or improvement or alleviation of elimination of symptoms and other indicators as are selected as appropriate measures by those skilled in the art. The conjugates disclosed herein can be administered in a single dose or in multiple doses.

In general, the active dose of conjugate for humans is in the range of from 1 ng/kg to about 20-100 mg/kg body weight per day, preferably about 0.01 mg to about 2-10 mg/kg body weight per day, in a regimen of a single dose or a one dose per day or twice or three or more times per day for a period of 1-4 weeks or longer.

The conjugates disclosed herein can be administered by any of the conventional routes of administration. The conjugates may be administered orally, subcutaneously or parenterally including intravenous, intraarterial, intramuscular, intraperitoneally, intraocular, ocular, otic, transtympanic and intranasal administration, intratracheal instillation and intratracheal inhalation, as well as infusion techniques. Implants of the conjugates may also be useful. It is to be emphasized that the pharmaceutical compositions of the invention are formulated to be compatible with their intended route of administration, suitable formulations and methods for their preparation will be apparent to those skilled in the art.

Liquid forms are prepared for invasive administration, e.g. injection or for topical or local or non-invasive administration. The term injection includes subcutaneous, transdermal, intravenous, intramuscular, intrathecal, intraocular, transtympanic and other parental routes of administration. The liquid compositions include aqueous solutions, with and without organic co-solvents, aqueous or oil suspensions, emulsions with edible oils, as well as similar pharmaceutical vehicles. According to some embodiments, the administration comprises intravenousadministration.

In some embodiments the compounds disclosed herein are formulated for non-invasive administration. In some embodiments the compounds disclosed herein are formulated as eardrops for topical administration to the ear. In some embodiments the compounds of the present invention are formulated as eye drops for topical administration to the surface of the eye. Further information on administration of the compounds of the present invention can be found in Tolentino et al., Retina 2004. 24:132-138; and Reich et al., Molecular Vision, 2003. 9:210-216. In addition, in certain embodiments the compositions for use in the treatments of the present invention are formed as aerosols, for example for intranasal administration. In certain embodiments the compositions for use in the treatments of the present invention are formed as nasal drops, for example for intranasal instillation. According to some embodiments the compositions are formulated as ear drops.

The therapeutic compositions disclosed herein are preferably administered into the lung by inhalation of an aerosol containing these compositions/compounds, or by intranasal or intratracheal instillation of said compositions. For further information on pulmonary delivery of pharmaceutical compositions see Weiss et al., Human Gene Therapy 1999. 10:2287-2293; Densmore et al., Molecular therapy 1999. 1:180-188; Gautam et al., Molecular Therapy 2001. 3:551-556; and Shahiwala & Misra, AAPS PharmSciTech 2004. 24; 6(3):E482-6. Additionally, respiratory formulations for siRNA are described in U.S. Patent Application Publication No. 2004/0063654.

In certain embodiments, oral compositions (such as tablets, suspensions, solutions) may be effective for local delivery to the oral cavity such as oral composition suitable for mouthwash for the treatment of oral mucositis.

In a particular embodiment, the conjugated dsRNA compounds disclosed herein are formulated for intravenous administration for delivery to the kidney for the treatment of kidney disorders, e.g. acute renal failure (ARF), delayed graft function (DGF) and diabetic retinopathy. It is noted that the delivery of the modified siRNA compounds according to the present invention to the target cells in the kidney proximal tubules is particularly effective in the treatment of ARF and DGF.

Delivery of compounds into the brain is accomplished by several methods such as, inter alia, neurosurgical implants, blood-brain barrier disruption, lipid mediated transport, carrier mediated influx or efflux, plasma protein-mediated transport, receptor-mediated transcytosis, absorptive-mediated transcytosis, neuropeptide transport at the blood-brain barrier, and genetically engineering "Trojan horses" for drug targeting. The above methods are performed, for example, as described in "Brain Drug Targeting: the future of brain drug development", W. M. Pardridge, Cambridge University Press, Cambridge, UK (2001).

In addition, in certain embodiments the conjugated dsRNA compositions for use in the treatments of the present invention are formed as aerosols, for example for intranasal administration. Intranasal delivery for the treatment of CNS diseases has been attained with acetylcholinesterase inhibitors such as galantamine and various salts and derivatives of galantamine, for example as described in US Patent Publication No. 2006/003989 and PCT Publication Nos. WO 2004/002402 and WO 2005/102275. Intranasal delivery of nucleic acids for the treatment of CNS diseases, for example by intranasal instillation of nasal drops, has been described, for example, in PCT Publication No. WO 2007/107789.

Methods of Treatment

In one aspect provided herein is a method of treating a subject suffering from a disorder associated with target gene expression comprising administering to the subject a therapeutically effective amount of a conjugated dsRNA compound of the invention. According to some embodiments the subject being treated is a warm-blooded animal and, in particular, mammal including human.

"Treating a subject" refers to administering to the subject a therapeutic substance effective to ameliorate symptoms associated with a disease, to lessen the severity or cure the disease, to slow down the progress of the disease, to prevent the disease from occurring or to postpone the onset of the disease to attenuate symptoms of the disease or disorder. "Treatment" refers to both therapeutic treatment and prophylactic or preventative measures, wherein the object is to prevent a disorder, to delay the onset of the disorder or reduce the symptoms of a disorder. Those in need of treatment include those already experiencing the disease or condition, those prone to having the disease or condition, and those in which the disease or condition is to be prevented. The conjugates disclosed herein are administered before, during or subsequent to the onset of the disease or condition.

According to some embodiments, the diseases or disorders to be treated by the conjugated dsRNA compounds of the present invention include without limitation apoptosis-related diseases; angiogenesis-related conditions; respiratory disorders; microvascular disorders; neovascular disorders; eye diseases and fibrotic disorder.

"Apoptosis-related disease" or "apoptosis-related condition" refers to a disease whose etiology is related either wholly or partially to the process of apoptosis. The disease may be caused either by a malfunction of the apoptotic process (such as in cancer or an autoimmune disease) or by over activity of the apoptotic process (such as in certain neurodegenerative diseases). Apoptosis is a significant mechanism in dry AMD, whereby slow atrophy of photoreceptor and pigment epithelium cells, primarily in the central (macular) region of retina takes place. Neuroretinal apoptosis is also a significant mechanism in diabetic retinopathy. It has been established that apoptosis contributes to neuronal loss in most neurodegenerative diseases.

"Angiogenesis-related condition" refers to any one of the medical conditions or disease states recognized to be influenced by angiogenesis or by an increase/decrease in angiogenesis of by the lack thereof, including conditions, which may be linked to angiogenesis in the future. Examples of such conditions include cancer, retinopathy, ischemia, macular degeneration, corneal diseases, glaucoma, diabetic retinopathy, stroke, ischemic heart disease, ulcers, scleradoma, myocardial infarction, myocardial angiogenesis, plaque neovascularization, ischemic limb angiogenesis, angina pectoris, unstable angina, coronary arteriosclerosis, arteriosclerosis obliterans, Berger's disease, arterial embolism, arterial thrombosis, cerebrovascular occlusion, cerebral infarction, cerebral thrombosis, cerebral embolism, inflammation, diabetic neovascularization, wound healing and peptic ulcer.

"Respiratory disorder" refers to conditions, diseases or syndromes of the respiratory system including but not limited to pulmonary disorders of all types including chronic obstructive pulmonary disease (COPD), emphysema, chronic bronchitis, asthma and lung cancer, inter alia. Emphysema and chronic bronchitis may occur as part of COPD or independently. In various embodiments the present invention provides methods and compositions useful in preventing or treating primary graft failure, ischemia-reperfusion injury, reperfusion injury, reperfusion edema, allograft dysfunction, pulmonary reimplantation response and/or primary graft dysfunction (PGD) after organ transplantation, in particular in lung transplantation, in a subject in need thereof.

"Microvascular disorder" refers to any condition that affects microscopic capillaries and lymphatics, in particular vasospastic diseases, vasculitic diseases and lymphatic occlusive diseases. Examples of microvascular disorders include, inter alia: eye disorders such as Amaurosis Fugax (embolic or secondary to SLE), apla syndrome, Prot CS and ATIII deficiency, microvascular pathologies caused by IV drug use, dysproteinemia, temporal arteritis, ischemic optic neuropathy (ION), anterior ischemic optic neuropathy (AION), optic neuritis (primary or secondary to autoimmune diseases), glaucoma, von Hippel Lindau syndrome, corneal disease, corneal transplant rejection cataracts, Eales' disease, frosted branch angiitis, encircling buckling operation, uveitis including pars planitis, choroidal melanoma, choroidal hemangioma, optic nerve aplasia; retinal conditions such as retinal artery occlusion, retinal vein occlusion, retinopathy of prematurity, HIV retinopathy, Purtscher retinopathy, retinopathy of systemic vasculitis and autoimmune diseases, diabetic retinopathy, hypertensive retinopathy, radiation retinopathy, branch retinal artery or vein occlusion, idiopathic retinal vasculitis, aneurysms, neuroretinitis, retinal embolization, acute retinal necrosis, Birdshot retinochoroidopathy, long-standing retinal detachment; systemic conditions such as Diabetes mellitus, diabetic retinopathy (DR), diabetes-related microvascular pathologies (as detailed herein), hyperviscosity syndromes, aortic arch syndromes and ocular ischemic syndromes, carotid-cavernous fistula, multiple sclerosis, systemic lupus erythematosus, arteriolitis with SS-A autoantibody, acute multifocal hemorrhagic vasculitis, vasculitis resulting from infection, vasculitis resulting from Behcet's disease, sarcoidosis, coagulopathies, neuropathies, nephropathies, microvascular diseases of the kidney, and ischemic microvascular conditions, inter alia.

Microvascular disorders may comprise a neovascular element. The term "neovascular disorder" refers to those conditions where the formation of blood vessels (neovascularization) is harmful to the patient. Examples of ocular neovascularization include: retinal diseases (diabetic retinopathy, diabetic Macular Edema, chronic glaucoma, retinal detachment, and sickle cell retinopathy); rubeosis iritis; proliferative vitreo-retinopathy; inflammatory diseases; chronic uveitis; neoplasms (retinoblastoma, pseudoglioma and melanoma); Fuchs' heterochromic iridocyclitis; neovascular glaucoma; corneal neovascularization (inflammatory, transplantation and developmental hypoplasia of the iris); neovascularization following a combined vitrectomy and lensectomy; vascular diseases (retinal ischemia, choroidal vascular insufficiency, choroidal thrombosis and carotid artery ischemia); neovascularization of the optic nerve; and neovascularization due to penetration of the eye or contusive ocular injury.

"Eye disease" refers to conditions, diseases or syndromes of the eye including but not limited to any conditions involving choroidal neovascularization (CNV), wet and dry AMD, ocular histoplasmosis syndrome, angiod streaks, ruptures in Bruch's membrane, myopic degeneration, ocular tumors, retinal degenerative diseases, ischemic neuropathies and retinal vein occlusion (RVO). In various embodiments, conditions disclosed herein, such as diabetic retinopathy, which are regarded as either a microvascular disorder or an eye disease, or both, under the definitions presented herein, are treated according to the methods of the present invention.

Fibrotic disorder includes fibrosis of the liver, lung, heart, kidney, bone marrow, eye, and uterine; systemic fibrosis and fibrosis resulting from injury or surgery. Fibrotic disorder includes liver fibrosis, hepatic damage, and liver cirrhosis; pulmonary fibrosis including lung fibrosis (including IPF idiopathic pulmonary fibrosis), any condition causing kidney fibrosis (e.g., CKD including ESRD), peritoneal fibrosis, fibrillogenesis, fibrotic diseases in other organs, abnormal scarring (keloids) associated with all possible types of skin injury accidental and jatrogenic (operations); scleroderma; cardiofibrosis, failure of glaucoma filtering operation; and intestinal adhesions.

More specifically, provided herein are methods and compositions useful in providing neuroprotection or treating a subject suffering from or susceptible to adult respiratory distress syndrome (ARDS); Chronic obstructive pulmonary disease (COPD); acute lung injury (ALI); Emphysema; Diabetic Neuropathy, nephropathy and retinopathy; diabetic macular edema (DME) and other diabetic conditions; Glaucoma; age related macular degeneration (wet or dry AMD); bone marrow transplantation (BMT) retinopathy; ischemic conditions; ocular ischemic syndrome (OIS); kidney disorders: acute renal failure (ARF), delayed graft function (DGF), transplant rejection; hearing disorders (including hearing loss); spinal cord injuries; oral mucositis; dry eye syndrome and pressure sores; neurological disorders arising from ischemic or hypoxic conditions, such as hypertension, hypertensive cerebral vascular disease, a constriction or obstruction of a blood vessel- as occurs in the case of a thrombus or embolus, angioma, blood dyscrasias, any form of compromised cardiac function including cardiac arrest or failure, systemic hypotension; stroke, disease, disorders and injury of the CNS, including, without being limited to, epilepsy, spinal cord injury, brain injury and neurodegenerative disorders, including, without being limited to Parkinson's disease, Amyotrophic Lateral Sclerosis (ALS, Lou Gehrig's Disease), Alzheimer's disease, Huntington's disease and any other disease-induced dementia (such as HIV-associated dementia for example).

The dsRNA conjugates of the present invention are useful in the treatment of cancer. The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia or lymphoid malignancies. Other examples of such cancers include kidney or renal cancer, breast cancer, colon cancer, rectal cancer, colorectal cancer, lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, liver cancer, bladder cancer, cancer of the peritoneum, hepatocellular cancer, gastric or stomach cancer including gastrointestinal cancer, gastrointestinal stromal tumors (GIST), pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, leiomyosarcomas, urinary tract carcinomas, thyroid carcinomas, Wilm's tumor, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. "Tumor", as used herein, refers to all neoplastic cell growth and proliferation, whether malignant or benign, and all pre-cancerous and cancerous cells and tissues.

In additional embodiments provided is a method of treating a subject suffering from or susceptible to any disease or disorder accompanied by an elevated level of a mammalian or non-mammalian target gene, the method comprising administering to the subject the dsRNA conjugate of the invention in a therapeutically effective dose thereby treating the subject.

Provided herein is the use of compounds which down-regulate the expression of a mammalian target gene particularly to double-stranded nucleic acid compounds useful in the treatment of the following diseases or conditions in which inhibition of the expression of the mammalian target gene is beneficial: ARDS; COPD; ALI; Emphysema; Diabetic Neuropathy, nephropathy and retinopathy; DME and other diabetic conditions; Glaucoma; AMD; BMT retinopathy; ischemic conditions including stroke; OIS; Neurodegenerative disorders such as Parkinson's disease, Alzheimer's disease, ALS; kidney disorders: ARF, DGF, transplant rejection; hearing disorders; spinal cord injuries; oral mucositis; cancer including hematopoietic and solid tumor cancer, dry eye syndrome and pressure sores. In another embodiment the compounds of the present invention are useful in organ storage and/or preservation before transplant.

According to some embodiments, the target gene to be downregulated by the conjugated dsRNA of the present invention include, without limitation a target gene is selected from the group consisting of p53 (TP53), TP53BP2, LRDD, CYBA, ATF3, CASP2 (Caspase 2), NOX3, HRK; C1QBP, BNIP3, MAPK8; Rac1, GSK3B, CD38, STEAP4, BMP2a; GJA1, TYROBP, CTGF, SPP1, RTN4R, ANXA2, RHOA, DUOX1, SLC5A1, SLC2A2, AKR1B1, SORD, SLC2A1, MME, NRF2, SRM, REDD2 (RTP801L), REDD1 (RTP801), NOX4, MYC, PLK1, ESPL1, HTRA2, KEAP1, p66, ZNHIT1, LGALS3, CYBB (NOX2), NOX1, NOXO1, ADRB1, HI 95, ARF1, ASPP1, SOX9, FAS, FASLG, Human MLL, AF9, CTSD, CAPNS1, CD80, CD86, HES1, HES5, CDKN1B, ID1, ID2, ID3, CDKN2A, Caspase 1, Caspase 3, Caspase 4, Caspase 5, Caspase 6, Caspase 7, Caspase 8, Caspase 9, Caspase 10, Caspase 12, Caspase 14, Apaf-1, Nod1, Nod2, Ipaf, DEFCAP, RAIDD, RICK, Bcl10, ASC, TUCAN, ARC, CLARP, FADD, DEDD, DEDD2, Cryopirin, PYC1, Pyrin, TRADD, UNC5a, UNC5b, UNC5c, ZUD, p84N5, LRDD, CDK1, CDK2, CDK4, CDK5, CDK9, PITSLRE A, CHK2, LATS1, Prk, MAP4K1, MAP4K2, STK4, SLK, GSK3alpha, GSK3beta, MEKK1, MAP3K5 (Ask1), MAP3K7, MAP3K8, MAP3K9, MAP3K10, MAP3K11, MAP3K12, DRP-1, MKK6, p38, JNK3, DAPK1, DRAK1, DRAK2, IRAK, RIP, RIP3, RIPS, PKR, IRE1, MSK1, PKCalpha, PKCbeta, PKCdelta, PKCepsilon, PKCeta, PKCmu, PKCtheta, PKCzeta, CAMK2A, HIPK2, LKB1, BTK, c-Src, FYN, Lck, ABL2, ZAP70, TrkA, TrkC, MYLK, FGFR2, EphA2, AATYK, c-Met, RET, PRKAA2, PLA2G2A, SMPD1, SMPD2, SPP1, FAN, PLCG2, IP6K2, PTEN, SHIP, AIF, AMID, Cytochrome c, Smac, HtrA2, TSAP6, DAP-1, FEM-, DAP-3, Granzyme B, DIO-1, DAXX, CAD, CIDE-A, CIDE-B, Fsp27, Ape1, ERCC2, ERCC3, BAP31, Bit1, AES, Huntingtin, HIP1, hSir2, PHAP1, GADD45b, GADD34, RAD21, MSH6, ADAR, MBD4, WW45, ATM, mTOR, TIP49, diubiquitin/FAT10, FAF1, p193, Scythe/BAT3, Amida, IGFBP-3, TDAG51, MCG10, PACT, p52/RAP, ALG2, ALG3, presenelin-1, PSAP, AIP1/Alix, ES18, mda-7, p14ARF, ANT1, p33ING1, p33ING2, p53AIP1, p53DINP1, MGC35083, NRAGE, GRIM19, lipocalin 2, glycodelin A, NADE, Porimin, STAG1, DAB2, Galectin-7, Galectin-9, SPRC, FLJ21908, WWOX, XK, DKK-1, Fzd1, Fzd2, SARP2, axin 1, RGS3, DVL1, NFkB2, IkBalpha, NF-ATC1, NF-ATC2, NF-ATC4, zf3/ZNF319, Egr1, Egr2, Egr3, Sp1, TIEG, WT1, Zac1, Icaros, ZNF148, ZK1/ZNF443, ZNF274, WIG1, HIVEP1, HIVEP3, Fliz1, ZPR9, GATA3, TR3, PPARG, CSMF, RXRa, RARa, RARb, RARg, T3Ra, Erbeta, VDR, GR/GCCR, p53, p73alpha, p63 (human [ta alpha, ta beta, ta gamma, da alpha, a beta, da gamma], 53BP2, ASPP1, E2F1, E2F2, E2F3, HIF1 alpha, TCF4, c-Myc, Max, Mad, MITF, Id2, Id3, Id4, c-Jun, c-Fos, ATF3, NF-IL6, CHOP, NRF1, c-Maf, Bach2, Msx2, Csx, Hoxa5, Ets-1, PU1/Spi1, Ets-2, ELK1, TEL1, c-Myb, TBX5, IRF1, IRF3, IRF4, IRF9, AP-2 1pha, FKHR, FOXO1A, FKHRL1, FOXO3a, AFX1, MLLT7, Tip60, BTG1, AUF1, HNRPD, TIA1, NDG1, PCBP4, MCG10, FXR2, TNFR2, LTbR, CD40, CD27, CD30, 4-1BB, TNFRSF19, XEDAR, Fn14, OPG, DcR3, FAS, TNFR1, WSL-1, p75NTR, DR4, DR5, DR6, EDAR, TNF 1pha, FAS ligand, TRAIL, Lymphotoxin alpha, Lymphotoxin beta, 4-1BBL, RANKL, TL1, TWEAK, LIGHT, APRIL, IL-1-alpha, IL-1-beta, IL-18, FGF8, IL-2, IL-21, IL-5, IL-4, IL-6, LIF, IL-12, IL-7, IL-10, IL-19, IL-24, IFN alpha, IFN beta, IFN gamma, M-CSF, Prolactinm, TLR2, TLR3, TLR4, MyD88, TRIF, RIG-1, CD14, TCR alpha, CD3 gamma, CD8, CD4, CD7, CD19, CD28, CTLA4, SEMA3A, SEMA3B, HLA-A, HLA-B, HLA-L, HLA-Dmalpha, CD22, CD33, CALL, DCC, ICAM1, ICAM3, CD66a, PVR, CD47, CD2, Thy-1, SIRPa1, CD5, E-cadherin, ITGAM, ITGAV, CD18, ITGB3, CD9, IgE Fc R beta, CD82, CD81, PERP, CD24, CD69, KLRD1, galectin 1, B4GALT1, C1q alpha, C5R1, MIP1alpha, MIP1beta, RANTES, SDF1, XCL1, CCCKR5, OIAS/OAS1, INDO, MxA, IFI16, AIM2, iNOS, HB-EGF, HGF, MIF, TRAF3, TRAF4, TRAF6, PAR-4, IKKGamma, FIP2, TXBP151, FLASH, TRF1, IEX-1S, Dok1, BLNK, CIN85, Bif-1, HEF1, Vav1, RasGRP1, POSH, Rac1, RhoA, RhoB, RhoC, ALG4, SPP1, TRIP, SIVA, TRABID, TSC-22, BRCA1, BARD1, 53BP1, MDC1, Mdm4, Siah-1, Siah-2, RoRet, TRIM35, PML, RFWD1, DIP1, Socs1, PARC, USP7, CYLD). Particular target genes include DDIT4, CDKN1B, RTP801 (REDD1), CASP2, p53, RhoA, TLR2, TLR4, Nox3, Hes5, Hes3, CAPNS, REDD2, and a NOX gene selected from NOX1, NOX2, NOX3, NOX4, NOX5, DUOX1, DUOX2, NOXO1, NOXO2 (p47phox, NCF1), NOXA1, NOXA2 (p67phox, NCF2), CYBA. Preferably, the target gene is selected from the group consisting of RhoA, DDIT4, CDKN1B and Myd88.

Other useful target genes are genes of microbial origin, for example bacterial, fungal, mycloplasma or viral.

Combination Therapy

The methods of treating the diseases disclosed herein include administering a conjugate disclosed herein in conjunction or in combination with at least one therapeutically active agent, for example an additional inhibitor, a substance which improves the pharmacological properties of the conjugated dsRNA compound, or an additional compound known to be effective in the treatment of a subject suffering from or susceptible to any of the hereinabove mentioned diseases and disorders. By "in conjunction with" or "in combination with" is meant that the at least one therapeutically active agent is administered prior to, simultaneously or subsequent to the conjugated dsRNA of the present invention.

In another aspect, provided are pharmaceutical compositions comprising a combination of the therapeutic conjugated dsRNA compound of the invention together with at least one additional therapeutically active agent. It is to be emphasized that the conjugated dsRNA of the invention and the additional therapeutically active agents may be formulated together in the same pharmaceutical formulation or in separate formulations. Appropriate doses of known therapeutic agents for use in combination with the conjugated dsRNA compounds of the invention are readily appreciated by those skilled in the art. As is the case for the conjugated dsRNA compounds of the invention, any additional therapeutic agent may be administered by any suitable administration route, for example, by oral, buccal, inhalation, sublingual, rectal, vaginal, transurethral, nasal, otic, ocular, topical, percutaneous (i.e., transdermal), or parenteral (including intravenous, intramuscular, subcutaneous, and intracoronary) administration. It is to be emphasized that the conjugated dsRNA and any additional therapeutic agent administered in combination with it may be administered by the same or different administration routes.

In some embodiments, a conjugated dsRNA compound of the invention and the second therapeutic agent are administered by the same route, either provided in a single composition as two or more different pharmaceutical compositions. However, in other embodiments, a different route of administration for the conjugated dsRNA compound of the invention and the second therapeutic agent is either possible or preferred. Persons skilled in the art are aware of the best modes of administration for each therapeutic agent, either alone or in combination.

In various embodiments, the conjugated dsRNA compounds of the invention are the main active component in a pharmaceutical composition.

In another aspects, provided are pharmaceutical compositions comprising two or more siRNA molecules for the treatment of a disease and for any of the diseases and conditions mentioned herein. In some embodiments the two or more dsRNA molecules or formulations comprising said molecules are admixed in the pharmaceutical composition in amounts that generate equal or otherwise beneficial activity. In certain embodiments the two or more dsRNA molecules are covalently or non-covalently bound, or joined together by a nucleic acid linker of a length ranging from 2-100, preferably 2-50 or 2-30 nucleotides.

In some embodiments the pharmaceutical compositions disclosed herein further comprise one or more additional siRNA molecule, which targets one or more additional gene. In some embodiments, simultaneous inhibition of said additional gene(s) provides an additive or synergistic effect for treatment of the diseases disclosed herein.

The treatment regimen according to the invention is carried out, in terms of administration mode, timing of the administration, and dosage, so that the functional recovery of the patient from the adverse consequences of the conditions disclosed herein is improved or so as to postpone the onset of a disorder. The treatment regimen according to the invention is carried out, in terms of administration mode, timing of the administration, and dosage, so that the functional recovery of the patient from the adverse consequences of the conditions disclosed herein is improved or so as to postpone the onset of a disorder. Effective concentrations of individual nucleic acid molecule in a cell may be about 1 femtomolar, about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

An appropriate dosage for a mammal may be from 0.01 mg to 1 g per kg of body weight (e.g., 0.1 mg, 0.25 mg, 0.5 mg, 0.75 mg, 1 mg, 2.5 mg, 5 mg, 10 mg, 25 mg, 50 mg, 100 mg, 250 mg, 500 mg, 1 mg, 2.5 mg, 5 mg, 10 mg, 25 mg, 50 mg, 100 mg, 250 mg, or 500 mg per kg).

Dosage levels of from about 0.01 mg to about 100 mg per kilogram of body weight per day are useful in the treatment of the above-indicated conditions. The amount of active ingredient that can be combined with a pharmaceutically acceptable carrier to produce a single dosage form varies depending upon the host treated and the particular mode of administration. Dosage unit forms generally contain between from about 0.1 mg to about 500 mg of an active ingredient. Dosage units may be adjusted for local delivery, for example for intravitreal delivery of for transtympanic delivery.

The invention has been described in an illustrative manner, and it is to be understood that the terminology used is intended to be in the nature of words of description rather than of limitation. Modifications and variations of the present invention are possible in light of the above teachings. It is, therefore, to be understood that within the scope of the appended claims, the invention can be practiced otherwise than as specifically described.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

Without further elaboration, it is believed that one skilled in the art can, using the preceding description, utilize the present invention to its fullest extent. The following preferred specific embodiments are, therefore, to be construed as merely illustrative, and not limitative of the claimed invention in any way.

Standard molecular biology protocols known in the art not specifically described herein are generally followed essentially as in Sambrook et al., *Molecular cloning: A laboratory manual*, Cold Springs Harbor Laboratory, New-York (1989, 1992), and in Ausubel et al., *Current Protocols in Molecular Biology*, John Wiley and Sons, Baltimore, Maryland (1988), and as in Ausubel et al., Current Protocols in Molecular Biology, John Wiley and Sons, Baltimore, Maryland (1989) and as in Perbal, A Practical Guide to Molecular Cloning, John Wiley & Sons, New York (1988), and as in Watson et al., Recombinant DNA, Scientific American Books, New York and in Birren et al (eds) Genome Analysis: A Laboratory Manual Series, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego, Calif. (1990). In situ (In cell) PCR in combination with Flow Cytometry is useful for detection of cells containing specific DNA and mRNA sequences (Testoni et al., Blood 1996, 87:3822.) Methods of performing RT-PCR are also well known in the art.

Cell Culture

Induction of hypoxia-like conditions: Where needed, cells are treated with $CoCl_2$ for inducing a hypoxia-like condition as follows: siRNA transfection is carried out in 10-cm plates (30-50% confluency) as described by Czauderna et al., 2003; Kretschmer et al., 2003. Briefly, siRNA are transfected into cells by adding a preformed 10× concentrated complex of GB and lipid in serum-free medium to cells in complete medium. The total transfection volume is 10 ml. The final lipid concentration is 1.0 µg/ml; the final siRNA concentration was 20 nM unless otherwise stated. Induction of the hypoxic responses is carried out by adding $CoCl_2$ (100 µM) directly to the tissue culture medium 24 h before lysis.

Example 1

6-[5,6,7,8-tetrahydronaphthalene-butyric-C6 (amide) Phosphoramidite (compound of formula V)

6-[5,6,7,8-tetrahydronaphthalene-butyric-C6 (amide) Phosphoramidite (compound of formula V) was provided by BioLab Ltd.

Example 2

6[(5,6,7,8-tetrahydronaphthalene)butyric amide]-SNHS

A known strategy for conjugation of oligonucleotides to terminal moieties is by modifying the oligonucleotide with a nucleophile—e.g., amine or thiol—and then react it with the corresponding N-hydroxy-succinimide (NHS) ester or maleimide of the desired moiety. However, an opposite approach can also be taken in which the oligonucleotide is modified with an electrophilic NHS ester and is conjugated while still on the support with a nucleophile—such as an amino-, hydrazide-, or hydroxylamine-modified label (On-Column labeling).

6[(5,6,7,8-tetrahydronaphthalene)butyric C6-amide]-SNHS as well as 6[(5,6,7,8-tetrahydronaphthalene)butyric C6-amide]-NHS were prepared using known in the art methods for the preparation of NHS esters.

Example 3

Synthesis of RNA Strands Comprising a Phenyl Analog

Sense and antiisense strands were kindly synthesized by BioSpring (Frankfurt, Germany). Conjugation of the 6[(5,6,7,8-tetrahydronaphthalene)butyric amide]-1-[[(2-cyano-ethyl)-(N,N-diisopropyl)]-phosphoramidite]-6-amino-hexan-1-ol (also referred to as THNB-C6-phosphoramidite-) at the 5'-end of the oligonucleotide, was achieved by coupling of the phosphoramidite to the growing oligonucleotide chain under standard phosphoramidite coupling conditions unless otherwise specified.

6[(5,6,7,8-tetrahydronaphthalene)butyric amide]-SNHS (specifically, 7-(4-5,6,7,8-Tetrahydro-naphthalen-2-yl-butyrylamino)-heptanoic acid 2,5-dioxo-3-sulfo-pyrrolidin-1-yl ester—alternatively referred to as THNB-C6-SNHS) is linked to an oligonucleotide modified with a nucleophilic amine group or a thiol group. The nucleophilic functional group reacts with the corresponding N-hydroxy-succinimide (NHS) ester or maleimide of the desired label to obtain the conjugated oligonucleotide according to certain aspects of the invention. Alternatively, a different synthesis approach can be taken in which the oligonucleotide is modified with an electrophilic NHS ester and is conjugated while still on the support with a nucleophile—such as an amino-, hydrazide-, or hydroxylamine-modified label (On-Column labeling).

Example 4

Mobility of THNB-Attached Sense Strands and Control Strands

Table 1 lists some of the sense strands ("F") and antisense ("R") strands synthesized, some of which include a tetrahydronaphtalene-butyric amide (THNB) 6 aminohexan-1-ol moiety (referred to as THNBc6 capping moiety), an inverted abasic or a C6 amino moiety covalently attached at the 5' terminus through a phosphate group.

TABLE 1

Exemplary siRNA strands synthesized:

| Oligo Name | Oligo Sequence |
|---|---|
| RHOA_58_R_1055<br>No 5' moiety | rA;rG;mA;rA;mC;rU;rG2p;rU;mA;rA;mC;<br>rU;mC;rU;mG;rC;mC;rA;mC;zc3p;zc3p$ |
| RHOA_58_F_1122<br>Inverted abasic | zidB;rG;rU;rG;rG;rC;rA;rG;rA;rG;rU;<br>mU;rA;mC;rA;rG;rU;mU;rC;rU;zc3p |
| RHOA_58_F_1221<br>THNB with c6 alkyl linker | zTHNBc6p;zc6p;rG;rU;rG;rG;rC;rA;rG;rA;<br>rG;rU;mU;rA;mC;rA;rG;rU;mU;rC;rU;zc3p |
| RHOA_58_F_1222<br>THNB with c6 alkyl linker | zTHNBc6p;z(CH$_2$CH$_2$O)3p;rG;rU;rG;rG;rC;rA;rG;<br>rA;rG;rU;mU;rA;mC;rA;rG;rU;mU;rC;rU;zc3p |
| RHOA_58_F_1223<br>amino c6 with c6 alkyl linker | zc6Np;zc6p;rG;rU;rG;rG;rC;rA;rG;rA;rG;<br>rU;mU;rA;mC;rA;rG;rU;mU;rC;rU;zc3p |
| RHOA_58_F_1224<br>amino c6 with PEG linker | zc6Np;z(CH$_2$CH$_2$O)3p ;rG;rU;rG;rG;rC;rA;rG;rA;<br>rG;rU;mU;rA;mC;rA;rG;rU;mU;rC;rU;zc3p |

The mobility of the siRNA conjugates listed in Table 1, was analyzed as follows: 1 ng of each dsRNA conjugate was loaded per lane on a polyacrylamide gel. Northern blot procedure was performed according to standard methods, with 20 h duration of exposure. As can be seen in FIG. 1, the presence of THNB-C6 moiety attached to the 5' terminus of the dsRNA compound was confirmed by observing the slower mobility of the THNBc6 conjugates (F1221, and F1222) on denatured gel, as compared to dsRNA compounds conjugated to inverted abasic (F1122) or C6 amino (F1223 and F1224) moieties.

Example 5
Stability of the dsRNA Conjugates According to Some Embodiments of the Invention The stability of several siRNA duplexes listed in Table 2 against degradation by nucleases was analyzed. Stability of the RhoA siRNA conjugates was analyzed in human plasma and the cytosol; the stability of the CDKN1B siRNA conjugates was analyzed in rat plasma and rat cerebrospinal fluid and the stability of the DDIT4 siRNA conjugates was analyzed in human plasma and rabbit vitreous.

TABLE 2

SiRNA duplexes synthesized ("F", and "R" represent the sense and antisense strands respectively).

| Duplex Name | OligoSequence (5'>3') |
|---|---|
| RhoA_58_S1867 | F-zidB;rG;rU;rG;rG;rC;rA;rG;rA;rG;rU;mU;rA;mC;rA;rG;rU;mU;rC;rU;zc3p<br>R-rA;rG;mA;rA;mC;rU;rG2p;rU;mA;rA;mC;rU;mC;rU;mG;rC;mC;rA;mC;zc3p;zc3p$ |
| RhoA_58_S1973 | F-zTHNBc6p;zc6p;rG;rU;rG;rG;rC;rA;rG;rA;rG;rU;mU;rA;mC;rA;rG;rU;mU;rC;rU;zc3p<br>R-rA;rG;mA;rA;mC;rU;rG2p;rU;mA;rA;mC;rU;mC;rU;mG;rC;mC;rA;mC;zc3p;zc3p$ |
| RhoA_58_S1974 | F-zTHNBc6p;z(CH$_2$CH$_2$O)3p;rG;rU;rG;rG;rC;rA;rG;rA;rG;rU;mU;rA;mC;rA;rG;rU;mU;rC;rU;zc3p<br>R-rA;rG;mA;rA;mC;rU;rG2p;rU;mA;rA;mC;rU;mC;rU;mG;rC;mC;rA;mC;zc3p;zc3p$ |
| RhoA_58_S1975 | F-zc6Np;zc6p;rG;rU;rG;rG;rC;rA;rG;rA;rG;rU;mU;rA;mC;rA;rG;rU;mU;rC;rU;zc3p<br>R-rA;rG;mA;rA;mC;rU;rG2p;rU;mA;rA;mC;rU;mC;rU;mG;rC;mC;rA;mC;zc3p;zc3p$ |
| RhoA_58_S1976 | F-zc6Np;z(CH$_2$CH$_2$O)3p;rG;rU;rG;rG;rC;rA;rG;rA;rG;rU;mU;rA;mC;rA;rG;rU;mU;rC;rU;zc3p<br>R-rA;rG;mA;rA;mC;rU;rG2p;rU;mA;rA;mC;rU;mC;rU;mG;rC;mC;rA;mC;zc3p;zc3p$ |
| RhoA_58_S709 | F-rG;rU;rG;rG;rC;rA;rG;rA;rG;rU;rU;rA;rC;rA;rG;rU;rU;rC;rU;zdT;zdT$<br>R-rA;rG;rA;rA;rC;rU;rG;rU;rA;rA;rC;rU;rC;rU;rG;rC;rC;rA;rC;zdT;zdT$ |
| CDKN1B_4_S2018 | F-rG;mC;rA;rA;rU;mU;rA;rG;rG;rU;rU;rU;rU;rU;mC;rC;rU;mU;rA;zc3p<br>R-mU;rA;rA;rG;rG;rA;rA2p;rA;rA;rA;rC;rC;mU;rA;rA;rU;mU;G;rC;zc3p;zc3p$ |
| CDKN1B_31_S2022 | F-mC;rA;rG;rC;rG;rC;rA;rA;rG;rU;rG;rG;rA;rA;rU2p;rU2p;rU2p;rC2p;rA2p;zc3p<br>R-mU;rG;rA;rA;rA;rU;rU2p;rC;mC;rA;rC;rU;mU;rG;mC;rG;rC;mU;rG;zc3p;zc3p$ |
| CDKN1B_31_S2074 | F-zidB;mC;rA;rG;rC;rG;rC;rA;rA;rG;rU;rG;rG;rA;rA;rU2p;rU2p;rU2p;rC2p;rA2p;zc3p<br>R-mU;rG;rA;rA;rA;rU;rU2p;rC;mC;rA;rC;rU;mU;rG;mC;rG;rC;mU;rG;zc3p;zc3p$ |
| CDKN1B_4_S2075 | F-zidB;rG;mC;rA;rA;rU;mU;rA;rG;rG;rU;rU;rU;rU;rU;mC;rCrU;mU;rAzc3p<br>R-mU;rA;rA;rG;rG;rA;rA2p;rA;rA;rA;rC;rC;mU;rA;rA;rU;mU;rG;rC;zc3p;zc3p$ |
| CDKN1B_4_S2076 | F-zc6Np;rG;mC;rA;rA;rU;mU;rA;rG;rG;rU;rU;rU;rU;rU;mC;rC;rU;mU;rA;zc3p<br>R-mU;rA;rA;rG;rG;rA;rA2p;rA;rA;rA;rC;rC;mU;rA;rA;rU;mU;rG;rC;zc3p;zc3p$ |
| CDKN1B_4_S2077 | F-zTHNBc6p;rG;mC;rA;rA;rU;mU;rA;rG;rG;rU;rU;rU;rU;rU;mC;rC;rU;mU;rA;zc3p<br>R-mU;rA;rA;rG;rG;rA;rA2p;rA;rA;rA;rC;rC;mU;rA;rA;rU;mU;rG;rC;zc3p;zc3p$ |
| DDIT4_41_S2071 | F-zidB;rC;rC;rC;rU;rC;rA;rG;rU;rA;rC;rU;rG;rU;rA;rG;mC;rA;mU;rA;zc3p<br>R-mU;rA;mU;rG;rC;rU2p;rA;mC;rA;rG;mU;rA;rC;rU;mG;rA;rG;rG;rG;zc3p;zc3p$ |

TABLE 2 -continued

SiRNA duplexes synthesized ("F", and "R" represent the sense and antisense strands respectively).

| Duplex Name | OligoSequence (5'>3') |
|---|---|
| DDIT4_41_S2072 | F-zc6Np;rC;rC;rC;rU;rC;rA;rG;rU;rA;rC;rU;rG;rU;rA;rG;mC;rA;mU;rA;zc3p<br>R-mU;rA;mU;rG;rC;rU2p;rA;mC;rA;rG;mU;rA;rC;rU;mG;rA;rG;rG;rG;zc3p;zc3p$ |
| DDIT4_41_S2073 | F-zTHNBc6p;rC;rC;rC;rU;rC;rA;rG;rU;rA;rC;rU;rG;rU;rA;rG;mC;rA;mU;rA;zc3p<br>R-mU;rA;mU;rG;rC;rU2p;rA;mC;rA;rG;mU;rA;rC;rU;mG;rA;rG;rG;rG;zc3p;zc3p$ |
| DDIT4_41_S2012 | F-rC;rC;rC;rU;mC;rA;rG;mU;rA;rC;mU;rG;mU;rA;rG;mC;rA;mU;rA;zc3p<br>R-mU;rA;mU;rG;rC;rU2p;rA;mC;rA;rG;mU;rA;rC;rU;mG;rA;rG;rG;rG;zc3p;zc3p$ |
| DDIT4_41_S2013 | F-rC;rC;rC;rU;rC;rA;rG;rU;rA;rC;rU;rG;rU;rA;rG;mC;rA;mU;rA;zc3p<br>R-mU;rA;mU;rG;rC;rU2p;rA;mC;rA;rG;mU;rA;rC;rU;mG;rA;rG;rG;rG;zc3p;zc3p$ |
| MYD88_11_S2134 | F-zidB;rG;rA;rA;rU;rG;rU;rG;rA;rC;rU;rU;rC;rC;rA;rG2p;rA2p;rC2p;rC2p;rA2p<br>R-mU;rG;rG;mU;mC;mU;rG;rG;mA;rA;rG;mU;mC;rA;mC;rA;mu;mu;mC;zc3p;zc3p$ |
| MYD88 1 | F-zTHNBc6p;rG;rA;rA;rU;rG;rU;rG;rA;rC;rU;rU;rC;rC;rA;rG2p;rA2p;rC2p;rC2p;rA2p<br>R-mU;rG;rG;mU;mC;mU;rG;rG;mA;rA;rG;mU;mC;rA;mC;rA;mU;mU;mC;zc3p;zc3p$ |

Figure 2A:
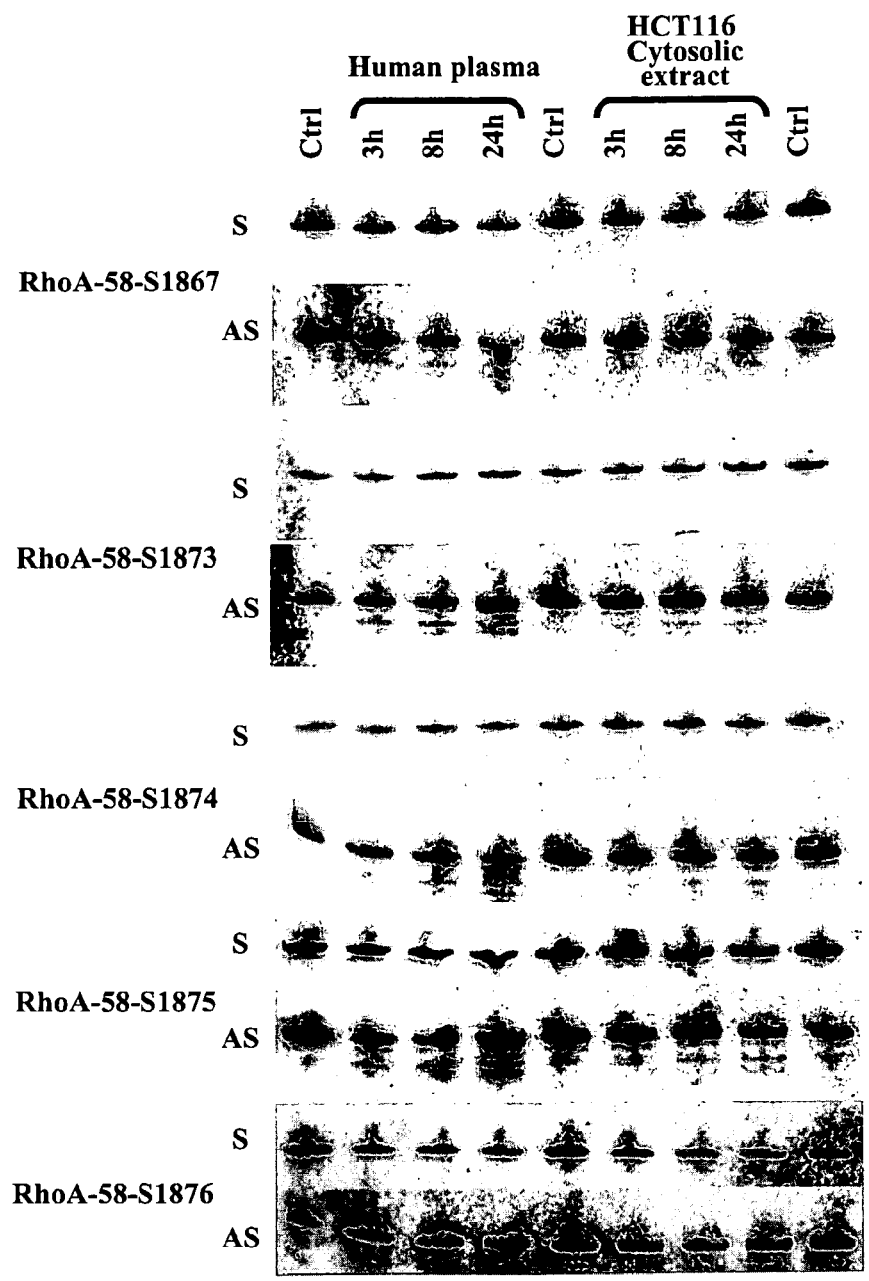
FIG. 2 depicts stability of THNBC6-conjugated targeted dsRNA; A: THNBC6-conjugated RhoA targeted dsRNA in human plasma and HCT116NN cytosolic extract; B: THNBC6-conjugated CDKN1B targeted dsRNA in rat plasma and rat cerebrospinal; and C: THNBC6-conjugated DDIT4 targeted dsRNA in human plasma and rabbit vitreous.
Figure 2B:
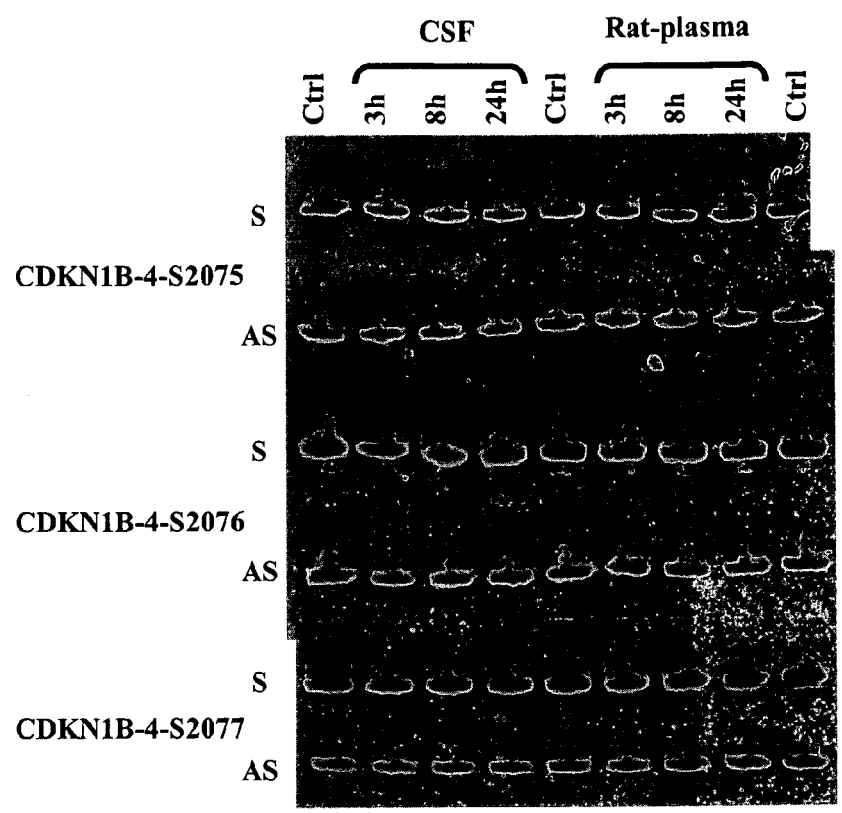
Figure 2C:
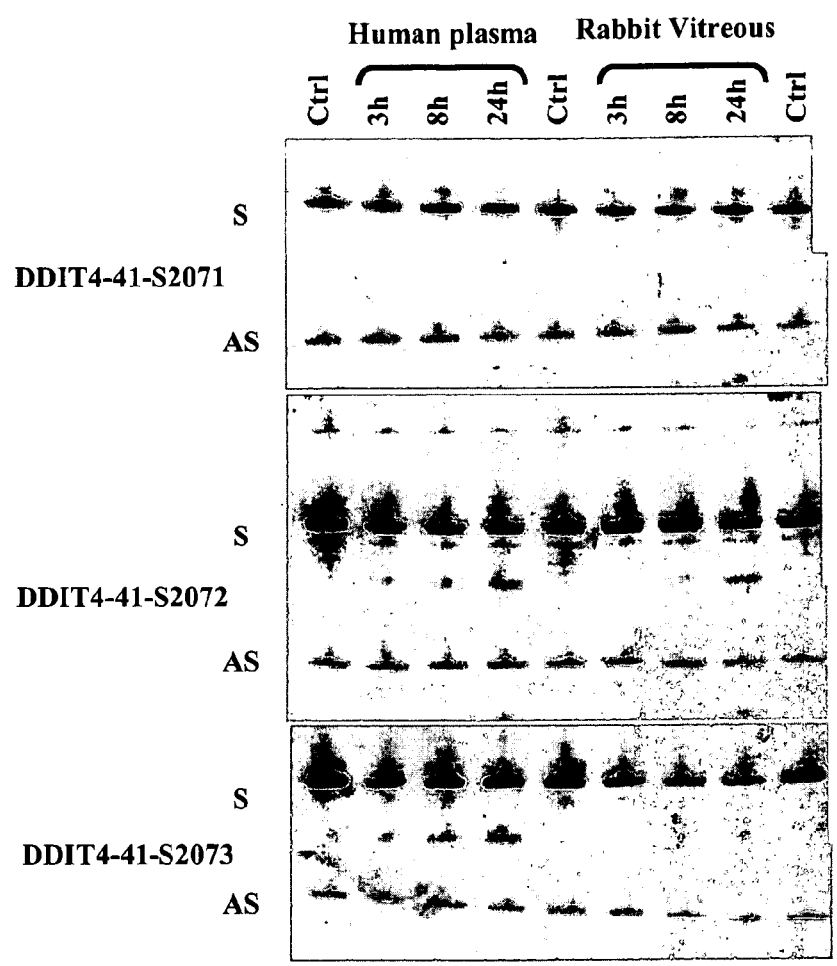

The siRNA duplexes synthesized were incubated for 24 hours at 37° C. in one or more of human plasma, HCT116 Cytosolic extract, rat plasma, rat cerebrospinal fluid or rabbit vitreous. At time points between 0 and 24 hours after incubation, 1 ng aliquots were transferred to TBE-loading buffer, snap frozen in liquid nitrogen and stored at −20° C. until use. The aliquots were thawed on ice and analyzed by non-denaturing polyacrylamide gel electrophoresis. Based on the gel migration patterns, presented in FIG. 2A, the RhoA siRNA duplexes tested, including the THNBc6 conjugated siRNA duplexes, were found to be stable for at least 24 hours at 37° C. in either human plasma or HCT116 Cytosolic extract. The CDKN1B siRNA duplexes were found to be stable for at least 24 hours at 37° C. in either rat plasma or rat cerebrospinal fluid (FIG. 2B) and the DDIT4 siRNA duplexes were found to be stable for at least 24 hours at 37° C. in either human plasma and in rabbit vitreous (FIG. 2C).

Example 6

Knockdown Activity of RhoA mRNA in HCT116 Cells

The RhoA siRNA duplexes listed in Table 2 were tested in cell culture by qPCR for their ability to elicit RhoA mRNA knockdown following transfection. Knockdown activity was measured at concentrations of 1, 5, 20, and 40 nM of the exemplary siRNA duplexes. The siRNA dose-dependent knockdown of RhoA mRNA in HCT116 cells (presented as RhoA mRNA concentration (% of control)) is summarized in Table 3. As can be seen, significant dose-dependent RhoA mRNA knockdown activity was demonstrated for all the duplexes tested. The modification of siRNA with THNBc6 did not affect the knockdown activity of the siRNA as compared to the activity of the unconjugated siRNA control (RhoA_58_S709).

TABLE 3

In vitro dose-dependent knockdown activity of RhoA mRNA in HCT116 cells transfected with siRNA modified duplexes according to some embodiments of the invention.

| DUPLEX NAME | CONCENTRATION (nM) | RhoA mRNA concentration (% of control) |
|---|---|---|
| RhoA_58_S1867 | 1 | 34 |
|  | 5 | 13 |
|  | 20 | 16 |
|  | 40 | 20 |
| RhoA_58_S1973 | 1 | 36 |
|  | 5 | 24 |
|  | 20 | 10 |
|  | 40 | 11 |
| RhoA_58_S1974 | 1 | 36 |
|  | 5 | 12 |
|  | 20 | 9 |
|  | 40 | 9 |
| RhoA_58_S1975 | 1 | 33 |
|  | 5 | 11 |
|  | 20 | 13 |
|  | 40 | 9 |
| RhoA_58_S1976 | 1 | 39 |
|  | 5 | 11 |
|  | 20 | 7 |
|  | 40 | 7 |
| RhoA_58_S709 | 1 | 25 |
|  | 5 | 12 |
|  | 20 | 9 |
|  | 40 | 9 |

Example 7

In-Vitro Knock-Down Activity of CDKN1B

Figure 3:
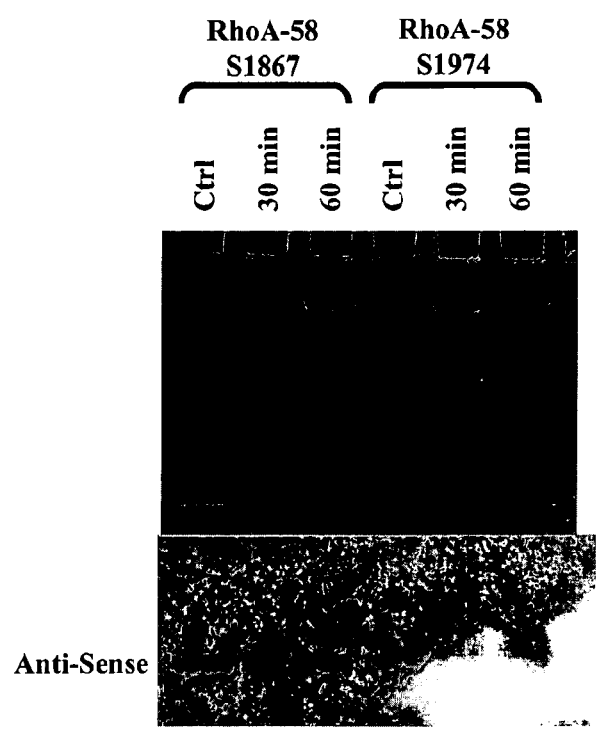
FIG. 3 depicts in-vitro knockdown activity of THNBC6-conjugated CDKN1B targeted dsRNA.

Knock-down activity of CDKN1B on cloned guinea pig gene in rat1 cells, with stable transfection, was studied using CDKN1B_4_S2074, CDKN1B_4_S2075 with idAb modification at the 5' terminus of the sense strand, CDKN1B_4_S2076 with Am-C6 modification at the 5' terminus of the sense strand, and CDKN1B_4_S2077 with THNBC6 modification at the 5' terminus of the sense strand as defined in Table 2, and CDKN1B_31_S2022 as follows. Control was Rat1-guinea pig-CDKN1B. Results are presented in FIG. 3. As can be seen, dose-dependent CDKN1B mRNA knockdown activity was demonstrated for the duplexes tested. The modification of siRNA with THNBc6 (CDKN1B_4_S2077) significantly improved the knockdown activity of the conjugated siRNA as compared to the activity of the siRNA duplexes not conjugated to the THNB-C6 moiety.

Example 8

Interaction of Human Plasma Proteins with THNBc6-Conjugated RhoA Targeted dsRNA The binding properties, in particular human plasma proteins binding selectivity, of the siRNA duplexes RhoA_58_S1867 and RhoA_58_1974 (an THNBC6 siRNA conjugate according to some embodiments of the invention) as defined above were analyzed.

Figure 4:
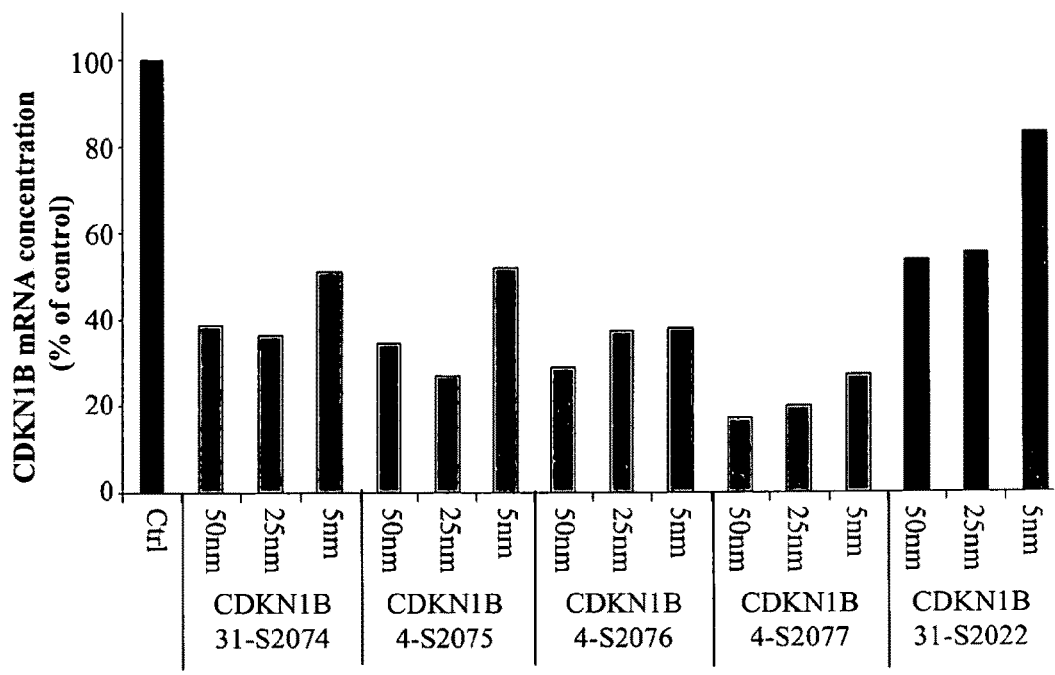
FIG. 4 depicts the interaction of h-plasma protein(s) with THNBC6-conjugated RhoA targeted dsRNA.

2 µl of the tested siRNA duplexes (10 µM) were incubated with 18 µl of human plasma at 37° C. Samples were collected after 30 minutes and after 60 minutes, equal volume of 0.5 Tris/Borate/EDTA (TBE) loading buffer was added, and 4 µl were loaded onto 12% native polyacrylamide gel (25 ng). The gel was run for 60 minutes at 100 V followed by "cooked native polyacrylamide gel" transfer procedure and hybridization to radioactively labeled oligonucleotide probes detecting either sense strands (antisense probe) of the dsRNA duplex. 25 ng dsRNA were dissolved in 5 uL PBS and loaded on native PAGE served as a migration reference for the intact dsRNA molecule. Results are presented in FIG. 4. The shift in the migration pattern of the THNB-C6 dsRNA conjugate may indicate binding of the conjugated dsRNA to plasma proteins. Specifically, the disappearance of the lower band (dsRNA unbound to plasma protein) upon incubation of the dsRNA with human plasma, indicates that most of the THNB-C6 conjugated dsRNA was bound to plasma proteins.

Example 9

On-Target and Off-Target Testing of THNBc6-Conjugated RhoA Targeted dsRNA

Off-target effects occur when a siRNA is processed by the RNA-Induced Silencing Complex (RISC) and down-regulates unintended targets. One of the main objectives when designing an siRNA is to develop strategies to minimize or even eliminate such down-regulation of unintended genes.

To test whether the siRNA of the invention has the potential to elicit unintended off-target effects, the activities of THNBc6-siRNA conjugates and control siRNAs were tested in the "guide-seed-sequence-and-passenger-strand-based off-target activity assay" using the psiCHECK™-2 (Promega™) plasmid construct. The psiCHECK™ system enables the evaluation of the intrinsic potency of both the guide strand (GS) (antisense) and the passenger strand (PS) (sense strand) to elicit targeted (on-target) and off-targeted effects, by monitoring the changes in expression levels of their target sequences. Two psiCHECK™-2-based constructs were prepared for the evaluation of target activity and potential off-target activity of each test molecule GS and PS strands. In each of the constructs one copy of the full target sequence of the test molecules PS or GS, was cloned into the multiple cloning site located downstream to the coding region of the *Renilla* luciferase translational stop codon in the 3'-UTR region. The activity of a siRNA toward this target sequence results either in cleavage and subsequent degradation of the fused mRNA or in translation inhibition of the encoded protein. In addition, the psiCHECK™-2 vector contains a second reporter gene, Firefly luciferase, transcribed under a different promoter, which allows for normalization of *Renilla* luciferase expression. The resulting vectors were termed:

PsiCHECH™2—GS-CM (guide strand, complete-match) vector containing a single copy of the GS (anti-sense) full target sequence (nucleotide sequence fully complementary to the whole 19-base sequence of the GS of the test molecule);

PsiCHECH™-2—PS-CM (passenger strand, complete-match) vector containing a single copy of the PS (sense) full target sequence (nucleotide sequence fully complementary to the whole 19-base sequence of the PS of the test molecule).

Guide strand or anti-sense strand: a strand of siRNA that enters the RISC complex and guides cleavage/silencing of the complementary RNA sequence Complete match: DNA fragment fully complementary to the guide strand of the siRNA. This DNA fragment is cloned in 3'UTR of a reporter gene and serves as a target for the straightforward RNA silencing.

Figure 5:
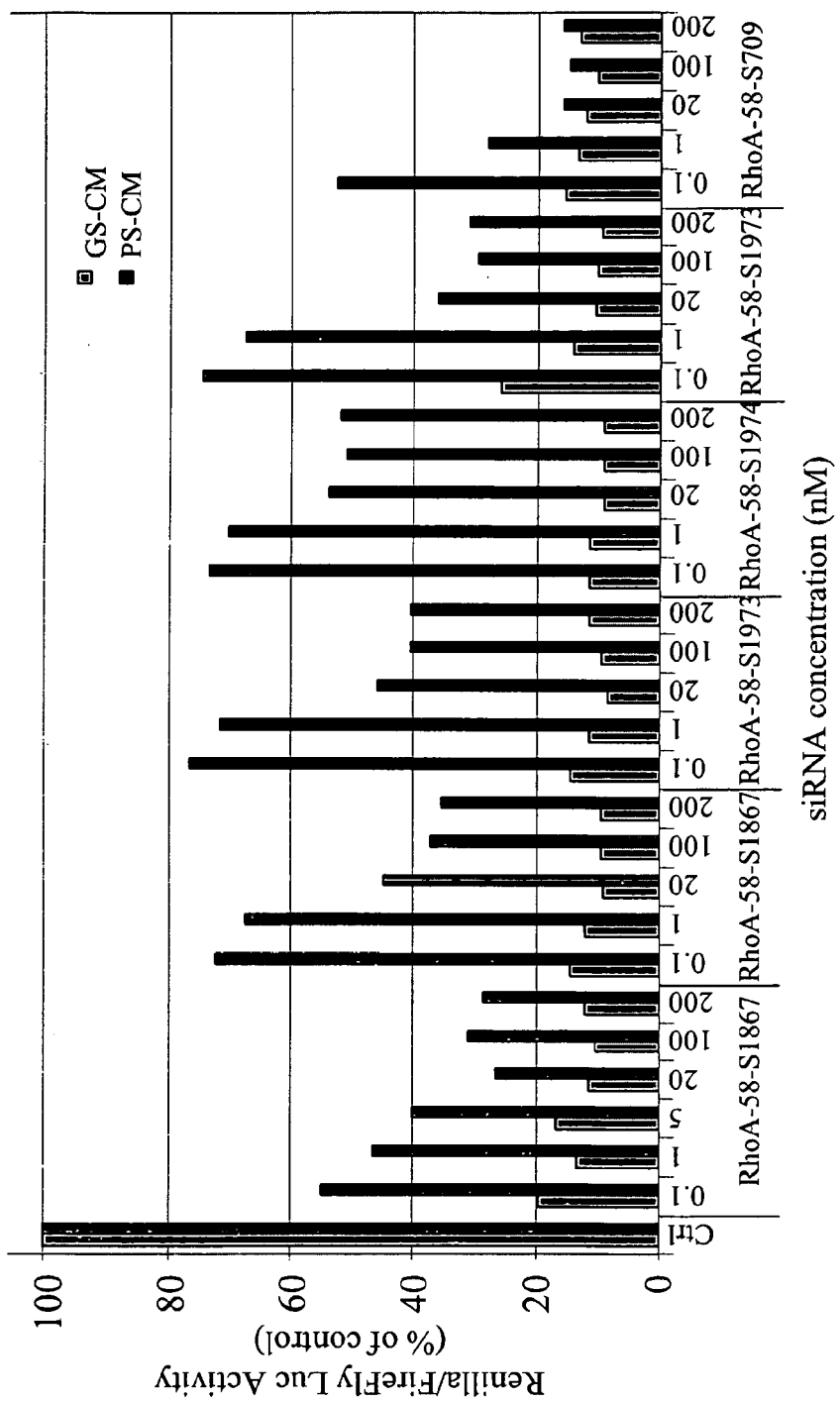
FIGS. 5, 6 and 7 depict the knockdown activity of the antisense and sense strands of THNBC6-conjugated RhoA, CDKN1B and DDIT4 targeted dsRNA compounds respectively measured using the "guide-seed-sequence-and-passenger-strand-based off target activity assay". Activity is expressed as the percentage of the normalized activity value in the tested sample relative to the normalized value obtained in cells transfected with the corresponding Psi-CHECH™-2 plasmid only but with no siRNA.

The different PsiCHECH™-2 plasmids were transfected into human HeLa cells. The transfected HeLa cells were then transfected with the siRNA of interest using Lipofectamine 2000 reagent. The final transfection concentrations of the RhoA-siRNA tested were 0.1, 1, 20, 100 and 200 nM. Duplicate transfections of each siRNA concentration were performed. 48 hours following siRNA transfection *Renilla* and FireFly Luciferase activities were measured in each of the siRNA transfected samples, using Dual-Luciferase® Assay kit according to the manufacturer procedure. *Renilla* Luciferase activity value was divided by Firefly Luciferase activity value for each sample (normalization) and activity was finally expressed as the percentage of the normalized activity value in the tested sample relative to the normalized value obtained in cells transfected with the corresponding PsiCHECH™-2 plasmid only but with no siRNA. The Knockdown activity of the antisense and sense strands were repeated twice. The average activity is presented in FIG. 5.

Clearly the conjugation of THNBC6 to the 5' terminus of the RhoA-siRNA reduces off-target activity as compared to the analogous unconjugated siRNA (RhoA-58-S709), while not affecting or improving on-target activity.

Example 10

On-Target and Off-Target Testing of CDKN1B Conjugates

Figure 6:
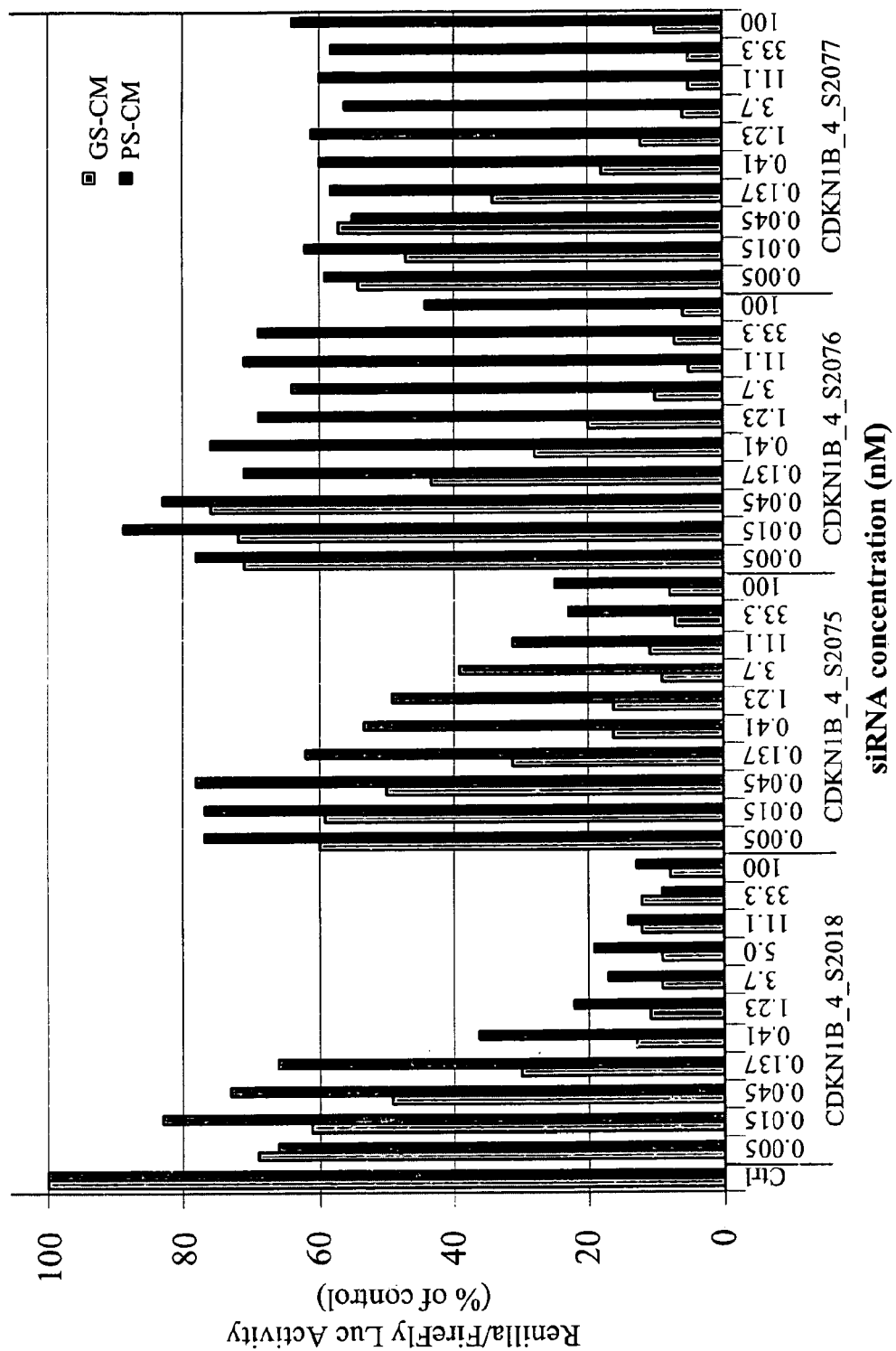

The psiCHECK™ system described above was used to study on-target and off-target knockdown activity of the CDKN1B conjugates, as described above. On-target and off-target knockdown activities of the antisense and conjugated sense strands of CDKN1B_4_S2075, CDKN1B_4_S2076 and CDKN1B_4_S2077 as well as CDKN1B_4_S2018 (non-conjugated (non-caped) CDKN1B siRNA compound used as control) were determined at final transfection concentrations of the CDKN1B-siRNA compounds of 0.005, 0.015, 0.045, 0.137, 0.41, 1.23, 3.7, 11.1, 33.3 and 100 nM. Results are presented in FIG. 6, expressed as the percentage of the normalized activity value in the tested sample relative to the normalized value obtained in cells transfected with the corresponding Psi-CHECH™-2 plasmid only but with no siRNA. As shown in the Table, significant dose-dependent knockdown activity is shown using all the conjugated duplexes tested, as compared to control.

Example 11

On-Target and Off-Target Testing of DDIT4 Conjugates

Figure 7:
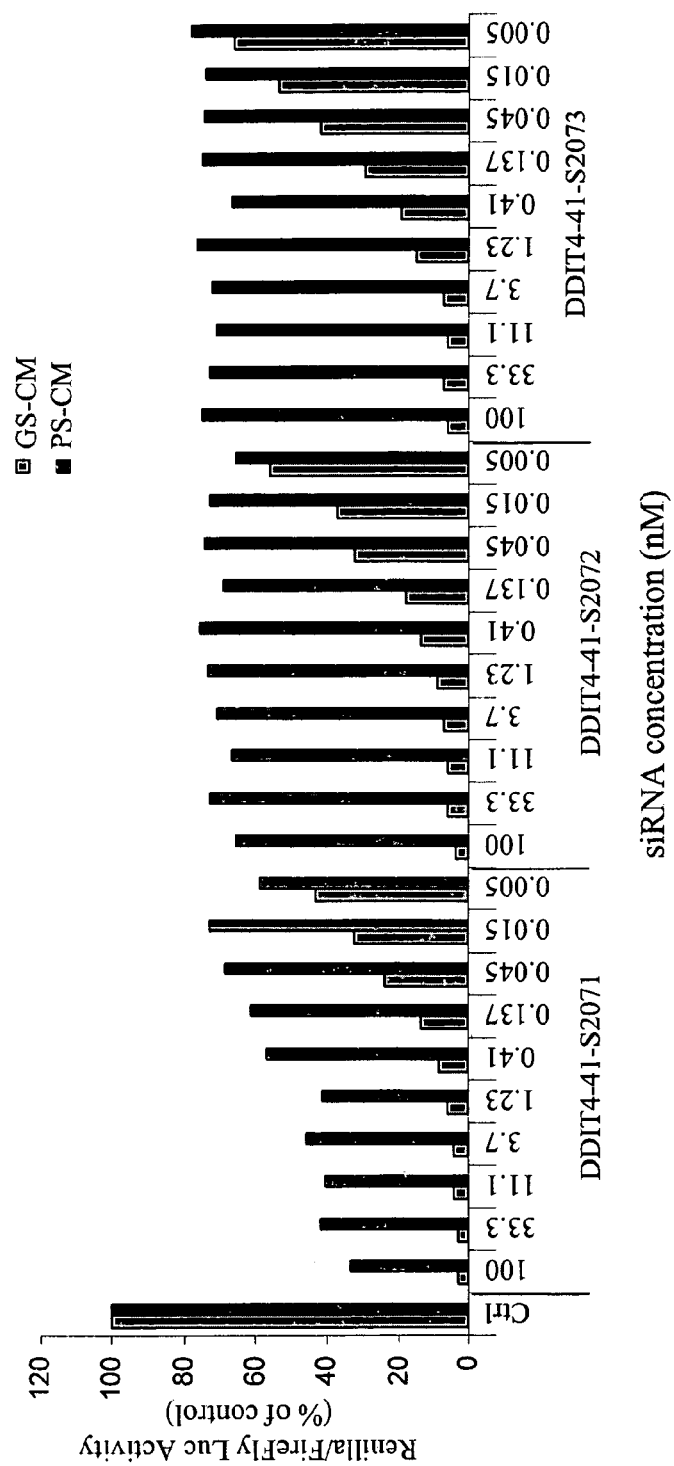

The psiCHECK™ system described above was used to study on-target and off-target knockdown activity, as described above. On-target and off-target activities of the antisense and sense strands of DDIT4_41_S2071, DDIT4_41_S2072, and DDIT4_41_S2073 were determined at final transfection concentrations of the DDIT4 siRNA compounds of 0.005, 0.015, 0.045, 0.137, 0.41, 1.23, 3.7, 11.1, 33.3 and 100 nM. On-target and off-target activities of the antisense and sense strands of DDIT4_41_S2012 and DDIT4_41_S2013 were determined at final transfection concentrations of 5 nM. Results are presented in FIG. 7, expressed as the percentage of the normalized activity value in the tested sample relative to the normalized value obtained in cells transfected with the corresponding Psi-CHECH™-2 plasmid only but with no siRNA. As can be seen in FIG. 7, significantly less knockdown activity was seen with the sense strand as compared to the antisense strand indicating reduced off-target activity for the tested siRNA conjugated at their 5' end to a THNBC6 or amino-C6 moieties.

Example 12

In Vivo Pharmacokinetic Studies

RhoA_58_S1974 and RhoA-_58_S1867 strands as defined above were annealed; the duplex was lyophilized and brought to a working concentration of 1 mg/ml in PBS. Vehicle PBS was used as negative control. The pharmacokinetic studies were performed using Male Sprague-Dawley rats at 8-10 weeks of age. Animals were provided with ad libitum commercial rodent diet and free access to drinking water, in environmentally controlled housing conditions. Acclimatization of at least 5 days was allowed.

A total of 6 animals were used, divided into 3 experimental groups of 2 animals per group as follows:

| Group no. | Group title | siRNA type | siRNA dose mg/kg | Blood collection, time after injection | Termination, hrs after injection |
|---|---|---|---|---|---|
| 1 | THNBC6-RHOA | RHOA_58_S1974 | 1 | 10', 30', 1 h, 2 h, 6 h, 24 h | 24 |
| 2 | RHOA | RHOA_58_S1867 | 1 | 10', 30', 1 h, 2 h, 6 h, 24 h | 24 |
| 3 | Intact | N/A | N/A | Any time | Any time |

Figure 8:
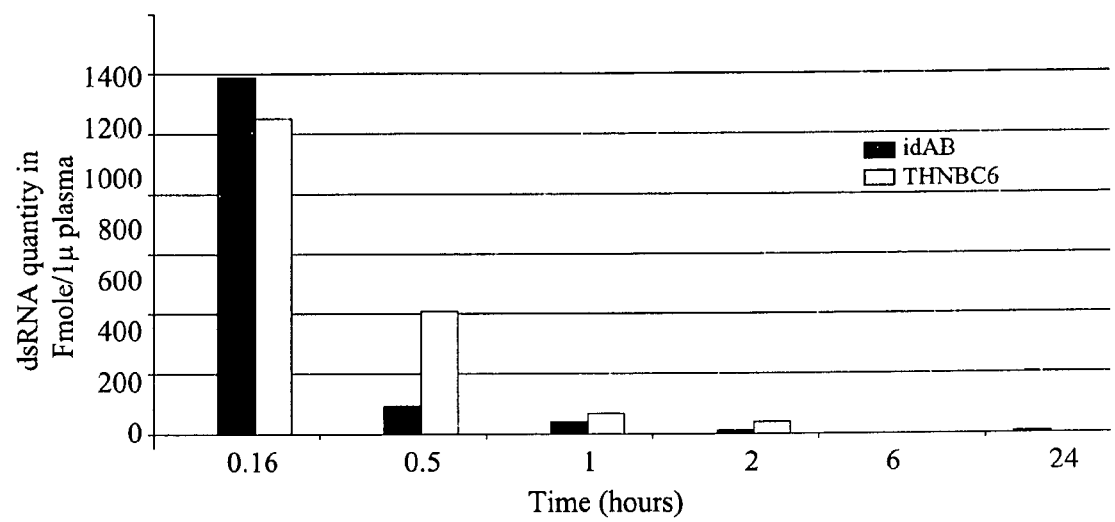
FIG. 8 depicts the variation of HNBC6-conjugated RhoA targeted dsRNA quantity in plasma with time.

THNBC6-conjugated and non-conjugated RHOA 58 siRNA were injected intravenously in a single injection at a dose of 1 mg/kg body weight to rats from groups 1 and 2, respectively. Group 3 served as intact control. Blood was collected from the tails of the animals of groups 1 and 2 at the indicated times. Following termination, blood plasma was subjected to qPCR for siRNA quantification. The experiment was repeated twice. The results are presented in Figure as an average of the dsRNA quantity (in Fmole/1 µl plasma) obtained for each group in duplicate experiments. As can be seen in FIG. 8, the THNB-C6 conjugated dsRNA displayed in increased blood circulation time as compared to the non-conjugated counterpart.

Example 13

In Vivo Pharmacokinetic Studies with MYD88 Targeted dsRNA

A dose of 20 µg of THNB conjugated MYD88_11_S2136 siRNA in 10 µL of PBS vehicle was microinjected into the vitreous body of adult, Sprague-Dawley rats. A control group was injected in the same manner with PBS vehicle. In addition siRNA, which induce immune response, was used as positive control. Study was terminated 24 hours after siRNA/vehicle administration.

Figure 9A:
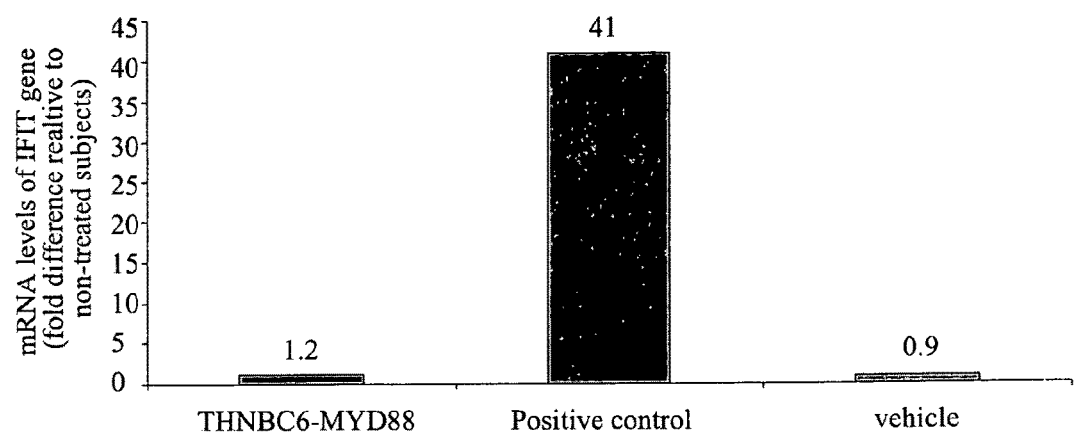
FIG. 9 depicts the variation in the levels of IFN-responsive genes IFIT (FIG. 9A) and MX1 (FIG. 9B) expressed as the fold difference relative to levels measured in non-treated subjects.
Figure 9B:
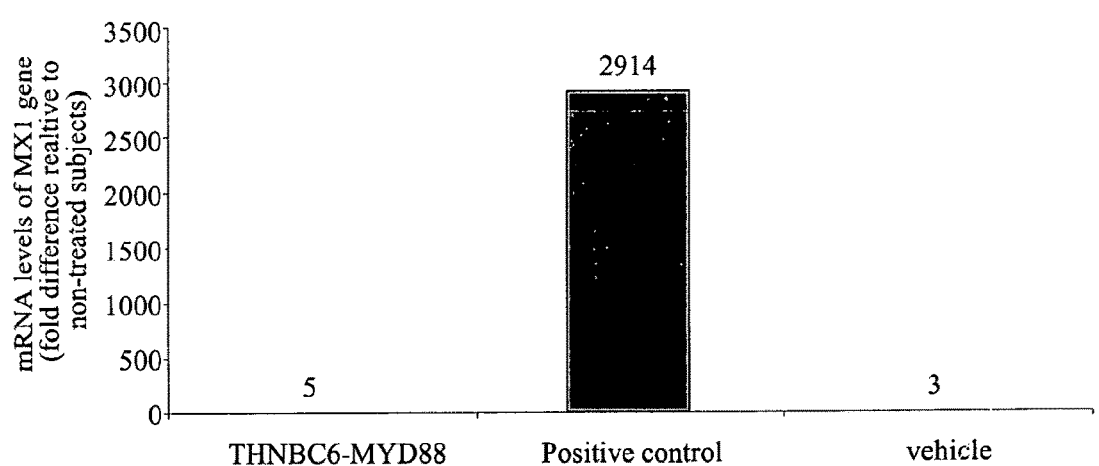

The retinas were collected and RNA was extracted using EZ extraction method. The extent of the interferon (IFN) response was also evaluated by measuring mRNA levels of genes involved in the IFN response (MX1 and IFIT1) using the IFNr qRT-primers system (InvivoGen). The levels of IFN-responsive genes were quantified using quantitative RT-PCR and expressed as the fold difference relative to levels measured in non-treated animals. As can be seen in FIGS. 9A and 9B the THNBC6 conjugated siRNA did not induce the IFN-responsive genes. In contrast, significant increases in the levels of IFN-responsive genes following treatment was observed with positive controls siRNA.

Figure 10:
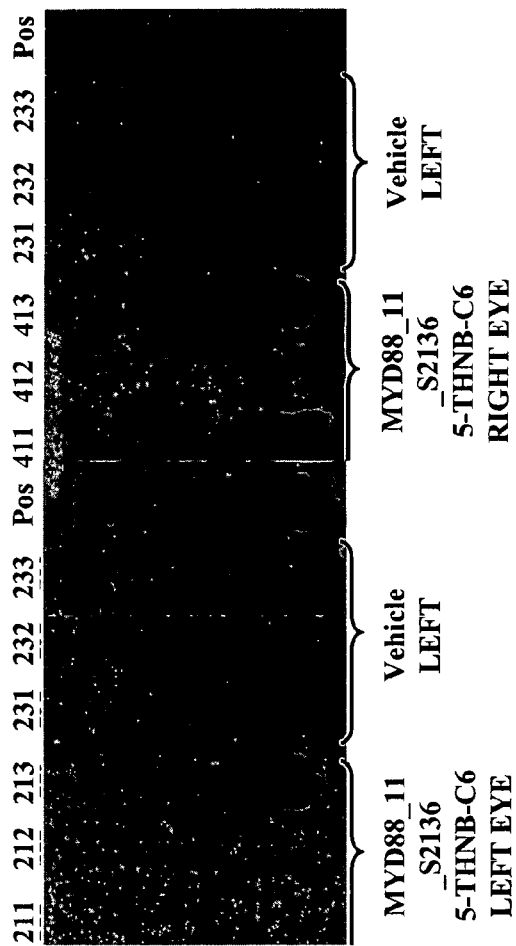
FIG. 10 depicts the RNAi-mediated cleavage of MYD88 mRNA in the rat eye following IVT administration of the THNBC6-conjugated MYD88 targeted dsRNA measured by the Rapid Amplification of cDNA Ends (RACE) method.

The RNAi-mediated cleavage of MYD88 mRNA in the rat eye following IVT administration of the THNBC6 conjugated siRNA was confirmed by Rapid Amplification of cDNA Ends (RACE). RNAi-mediated cleavage of a target mRNA occurs between nucleotides complementary to bases 10-11 of the siRNA guide strand to produce two mRNA fragments: a 5' fragment representing the region upstream to the cleavage site and the 3'-fragment representing the region downstream to the cleavage site. The presence of the downstream fragment can be detected using the RACE method, which is based on the ligation of an oligonucleotide adapter to the 5' end of this fragment, followed by PCR amplification using adapter-specific forward and gene-specific reverse primers. RNA was extracted from whole retina of rat eyes 24 hours after intravitreal (IVT) injection of 20 µg THNBC6 conjugated siRNA and subjected to RACE analysis. Amplification product was separated by agarose gel electrophoresis and visualized by Ethidium bromide staining. The separated products were analyzed by Southern blot hybridization as using a probe specific for the predicted RACE cleavage junction. Hybridization results indicate the specific generation of the proper product predicted for RNAi-mediated cleavage of MYD88 mRNA in THNB siRNA conjugate injected rat retina (FIG. 10).

Table 4 hereinbelow provides a legend of the modified ribonucleotides/unconventional moieties utilized in preparing the dsRNA molecules disclosed herein.

TABLE 4

Legend

| Code | Modification |
|---|---|
| Nuc | |
| 5medG | 5-methyl-deoxyriboguanosine-3'-phosphate |
| c6Np | Amino modifier C6 (Glen Research 10-1906-xx) |
| dA | deoxyriboadenosine-3'-phosphate |
| dB | abasic deoxyribose-3'-phosphate |
| dC | deoxyribocytidine-3'-phosphate |
| dG | deoxyriboguanosine-3'-phosphate |
| dT | thymidine-3'-phosphate |
| dT$ | thymidine (no phosphate) |
| enaA$ | ethylene-bridged nucleic acid adenosine (no phosphate) |
| enaC | ethylene-bridged nucleic acid cytidine 3' phosphate |
| enaG | ethylene-bridged nucleic acid guanosine 3' phosphate |
| enaT | ethylene-bridged nucleic acid thymidine 3' phosphate |
| iB | inverted deoxyabasic |
| LdA | L-deoxyriboadenosine-3'-phosphate (mirror image dA) |
| LdA$ | L-deoxyriboadenosine (no phosphate) (mirror image dA) |
| LdC | L-deoxyribocytidine-3'-phosphate (mirror image dC) |
| LdC$ | L-deoxyribocytidine (no phosphate) (mirror image dC) |
| LdG | L-deoxyriboguanosine-3'-phosphate (mirror image dG) |
| LdT | L-deoxyribothymidine-3'-phosphate (mirror image dT) |
| LdT$ | L-deoxyribothymidine (no phosphate) (mirror image dT) |
| mA | 2'-O-methyladenosine-3'-phosphate |
| mA$ | 2'-O-methyladenosine (no phosphate) |
| mC | 2'-O-methylcytidine-3'-phosphate |
| mC$ | 2'-O-methylcytidine (no 3'-phosphate) |
| mG | 2'-O-methylguanosine-3'-phosphate |
| mG$ | 2'-O-methylguanosine (no phosphate) |
| mU | 2'-O-methyluridine-3'-phosphate |
| mU$ | 2'-O-methyluridine (no phosphate) |
| rA | riboadenosine-3'-phosphate |
| rA$ | riboadenosine (no phosphate) |
| rA2p | riboadenosine-2'-phosphate |
| rC | ribocytidine-3'-phosphate |
| rC$ | ribocytidine (no phosphate) |
| rC2p | ribocytidine-2'-phosphate |
| rG | riboguanosine-3'-phosphate |
| rG2p | riboguanosine-2'-phosphate |
| rU | ribouridine-3'-phosphate |
| rU$ | ribouridine (no phosphate) |
| rU2p | ribouridine-2'-phosphate |
| p | 5'-phosphate |
| z | Prefix for Capping moiety |
| zc3p | C3Pi covalently attached |
| zc3p$ | C3OH covalently attached |
| $ | No terminal phosphate |

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

It will be readily apparent to one skilled in the art that varying substitutions and modifications can be made to the invention disclosed herein without departing from the scope and spirit of the invention. Thus, such additional embodiments are within the scope of the present invention and the following claims. The present invention teaches one skilled in the art to test various combinations and/or substitutions of chemical modifications described herein toward generating nucleic acid constructs with improved activity for mediating RNAi activity. Such improved activity can include improved stability, improved bioavailability, and/or improved activation of cellular responses mediating RNAi. Therefore, the specific embodiments described herein are not limiting and one skilled in the art can readily appreciate that specific combinations of the modifications described herein can be tested without undue experimentation toward identifying nucleic acid molecules with improved RNAi activity.

The inventions illustratively described herein may suitably be practiced in the absence of any element or elements, limitation or limitations, not specifically disclosed herein. Thus, for example, the terms "a" and "an" and "the" and similar referents in the context of describing the invention (especially in the context of the following claims) are to be construed to cover both the singular and the plural, unless otherwise indicated herein or clearly contradicted by context. The terms "comprising", "having," "including," "containing", etc. shall be read expansively and without limitation (e.g., meaning "including, but not limited to"). Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

Other embodiments are set forth within the following claims.

The invention claimed is:

1. A double-stranded ribonucleic acid (dsRNA) compound comprising a sense strand and an antisense strand wherein the sense strand, the antisense strand or both are covalently bound directly or via a linker to a moiety comprising a phenyl hydrocarbyl group, the moiety represented by the general formula I:

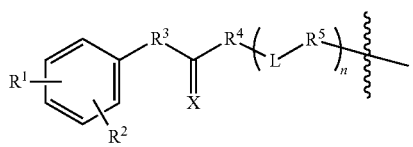

wherein
$R^1$ and $R^2$ together with the carbons to which they are attached form a substituted or unsubstituted $C_3$-$C_8$ cycloalkyl;
$R^3$ is a C1-C8 hydrocarbyl group optionally interrupted by up to 2 heteroatoms selected from oxygen, nitrogen or sulfur;
$R^4$ is NH, O, S or $CR^6R^7$;
$R^6$ and $R^7$ each is independently selected from the group consisting of H and a $C_1$-$C_4$ hydrocarbyl group;
x is O or S;
each L in said (L-$R^5$) groups is independently selected from the group consisting of a peptidyl chain of up to 12 amino acid residues, —[$CH_2$—$CH_2$—O]$_m$—, $R^8$O—, a $C_1$-$C_{12}$ hydrocarbyl group optionally interrupted by up to 2 heteroatoms selected from O, N or S;
$R^8$ is a C1-C12 hydrocarbyl group optionally interrupted by up to 2 heteroatoms selected from O, N or S;
n is an integer of 0 to 10;
m is an integer of 1 to 10;
each $R^5$ in each (L-$R^5$ groups) is independently selected from the group consisting of —P(O)($R^9$)—O—, —C(O)NH—, —O—; —NH—, —S—, —C(O)—; —C(O)O—; —NHCS—; —NHCO— and a single bond;
$R^9$ is selected from the group consisting of O$^-$, S$^-$, $BH_3^-$, $NR^6R^7$ and $CH_3$;
or a pharmaceutically acceptable salt thereof;
wherein the sense strand has sequence identity to a consecutive segment of a mRNA corresponding to a target gene.

2. The double-stranded ribonucleic acid compound of claim 1, wherein the moiety of formula (I) is bound directly or via a linker to a sugar moiety, backbone or base of a terminal nucleotide or nucleotide analog of the strand in which it is present.

3. The double-stranded ribonucleic acid compound of claim 2, wherein the terminal nucleotide or nucleotide analogue is selected from the group consisting of the 3' terminal or 5' terminal nucleotide or nucleotide analog of the sense strand and the 3' terminal nucleotide or nucleotide analog of the antisense strand.

4. The double-stranded ribonucleic acid compound of claim 1, wherein X in formula (I) is O.

5. The double-stranded ribonucleic acid compound of claim 1, wherein $R^4$ in formula (I) is NH.

6. The double-stranded ribonucleic acid compound of claim 1, wherein R3 in formula (I) is C3 alkyl.

7. The double-stranded ribonucleic acid compound of claim 1, wherein $R^1$ and $R^2$ in formula (I) together with the carbons to which they are attached form C6 cycloalkyl.

8. The double-stranded ribonucleic acid compound of claim 7, represented by the general formula (II):

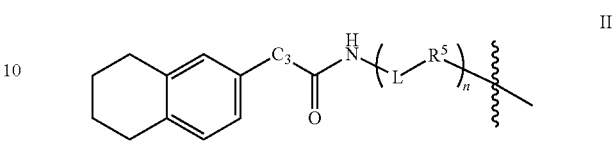

9. The double-stranded ribonucleic acid compound of claim 1, wherein n is 0.

10. The double-stranded ribonucleic acid compound of claim 1, wherein L is $R^8$O—.

11. The double-stranded ribonucleic acid compound of claim 10, wherein $R^8$ is a C6 alkyl.

12. The double-stranded ribonucleic acid compound of claim 1, wherein n is 1-10.

13. The double-stranded ribonucleic acid compound of claim 12, wherein $R^5$ is —P(O)($R^9$)—O—.

14. The double-stranded ribonucleic acid compound of claim 13, wherein the moiety of formula (I) is directly linked to the 3' terminal or 5' terminal nucleotide or nucleotide analog of the sense strand or to the 3' terminal nucleotide or nucleotide analog of the antisense strand of the dsRNA.

15. A double-stranded ribonucleic acid (dsRNA) compound comprising a sense strand and an antisense strand wherein the sense strand, the antisense strand or both are covalently bound directly or via a linker to a moiety comprising a phenyl hydrocarbyl group, the moiety represented by the general formula I:

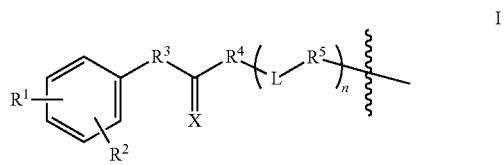

wherein
$R^1$ and $R^2$ each is independently selected from the group consisting of H, halogen, $C_1$-$C_{10}$ hydrocarbyl group, OR$^6$, OCOR$^6$, COOR$^6$, CH$_2$OR$^6$, CHO, COR$^6$, NR$^6$R$^7$ and SR$^6$; or $R^1$ and $R^2$ together with the carbons to which they are attached form a saturated or unsaturated cyclic $C_3$-$C_8$ hydrocarbyl ring optionally interrupted by up to 2 heteroatoms selected from oxygen, nitrogen or sulfur and the ring is optionally substituted by up to 3 groups independently selected from the group consisting of halogen, $C_1$-$C_3$ hydrocarbyl group, OR$^6$, OCOR$^6$, COOR$^6$, CH$_2$OR$^6$, CHO, COR$^6$, NR$^6$R$^7$, SR$^6$, =O, =S and =NH;
$R^3$ is a C1-C8 hydrocarbyl group optionally interrupted by up to 2 heteroatoms selected from oxygen, nitrogen or sulfur;
$R^4$ is NH, O, S or $CR^6R^7$;
$R^6$ and $R^7$ each is independently selected from the group consisting of H and a $C_1$-$C_4$ hydrocarbyl group;
X is O or S;
each L in said (L-$R^5$) groups is independently selected from the group consisting of a peptidyl chain of up to 12 amino acid residues, —[CH$_2$—CH$_2$—O]$_m$—, R$^8$O—, a C$_1$-C$_{12}$ hydrocarbyl group optionally interrupted by up to 2 heteroatoms selected from O, N or S;

R$^8$ is a C1-C12 hydrocarbyl group optionally interrupted by up to 2 heteroatoms selected from O, N or S;

n is an integer of 1 to 10;

m is an integer of 1 to 10;

R$^5$ in each (L-R$^5$ group) is —P(O)(R$^9$)—O—;

or a pharmaceutically acceptable salt thereof;

wherein the sense strand has sequence identity to a consecutive segment of a mRNA corresponding to a target gene, wherein the moiety of formula (I) is directly linked to the 3' terminal or 5' terminal nucleotide or nucleotide analog of the sense strand or to the 3' terminal nucleotide or nucleotide analog of the antisense strand of the dsRNA, wherein the moiety of formula (I) is linked to the 5' terminal nucleotide of the sense strand, and the sense strand of the double stranded ribonucleic acid compound is represented by the general formula III:

III

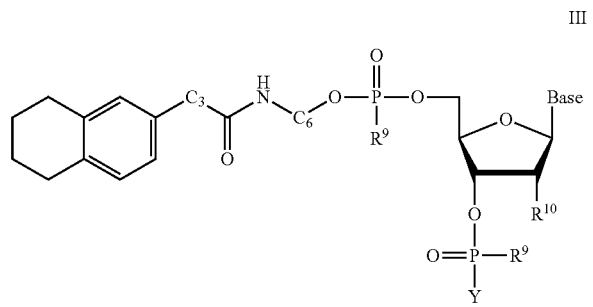

wherein Y is an oligonucleotide of about 14 to 39 nucleotides in length, linked to the 5'O of the adjacent nucleotide;

wherein Base is adenine, guanine, cytosine, uracil or an analog thereof; and wherein R$^{10}$ is selected from the group consisting of H, OH, OR$^6$, NR$^6$R$^7$ and OR$^6$OR$^7$.

16. The double-stranded ribonucleic acid compound of claim 1, moiety of formula (I) is bound to the sense strand, antisense strand or both via a linker, the linker is selected from the group consisting of a carbon linker, a peptide linker, a nucleotide linker, an amido alkyl linker, a phosphodiester linker and a phosphorothioate linkage.

17. The double-stranded ribonucleic acid compound of claim 1, wherein the target gene is a human, bacterial or viral target gene.

18. The double-stranded ribonucleic acid compound of claim 17, wherein the human target gene is selected from the group consisting of DDIT4, CDKN1B, MYD88, RTP801 (REDD1), CASP2, p53, RhoA, TLR2, TLR4, Nox3, Hes5, Hes3, CAPNS, REDD2, and a NOX gene selected from NOX1, NOX2, NOX3, NOX4, NOX5, DUOX1, DUOX2, NOXO1, NOXO2 (p47phox, NCF1), NOXA1, NOXA2 (p67phox, NCF2) and CYBA.

19. A pharmaceutical composition comprising the double-stranded ribonucleic acid compound of claim 1, and a pharmaceutically acceptable carrier.

* * * * *